(12) United States Patent
Massoudi

(10) Patent No.: US 10,080,588 B2
(45) Date of Patent: Sep. 25, 2018

(54) SPINAL IMPLANT DEVICE WITH FIXATION PLATES AND METHOD OF IMPLANTING

(71) Applicant: Farzad Massoudi, Corona Del Mar, CA (US)

(72) Inventor: Farzad Massoudi, Corona Del Mar, CA (US)

( * ) Notice: Subject to any disclaimer, the term of this patent is extended or adjusted under 35 U.S.C. 154(b) by 0 days.

(21) Appl. No.: 14/267,492

(22) Filed: May 1, 2014

(65) Prior Publication Data

US 2014/0243897 A1 Aug. 28, 2014

Related U.S. Application Data

(60) Continuation of application No. 13/927,480, filed on Jun. 26, 2013, which is a division of application No. 13/033,450, filed on Feb. 23, 2011, now Pat. No. 8,496,689.

(51) Int. Cl.
*A61B 17/70* (2006.01)

(52) U.S. Cl.
CPC ...... *A61B 17/7067* (2013.01); *A61B 17/7064* (2013.01); *A61B 17/7068* (2013.01)

(58) Field of Classification Search
CPC .................. A61B 17/7062–17/707; A61B 17/8052–17/8057
See application file for complete search history.

(56) References Cited

U.S. PATENT DOCUMENTS

| 5,011,484 A | 4/1991 | Breard |
| 5,558,674 A | 9/1996 | Heggeness et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |

(Continued)

FOREIGN PATENT DOCUMENTS

| WO | WO2010019783 | 2/2010 |
| WO | WO2011019756 | 2/2011 |

OTHER PUBLICATIONS

Copenheaver, Blaine R., PCT International Search Report, dated Jul. 2, 2012, pp. 1-6.

(Continued)

*Primary Examiner* — Jan Christopher Merene
*Assistant Examiner* — Steven Cotroneo
(74) *Attorney, Agent, or Firm* — Stetina Brunda Garred and Brucker

(57) ABSTRACT

There is provided a spinal implant device for placement between adjacent spinous processes and a pair of opposing facet joints. The spinal implant device includes a fusion cage, first and second fixation plates and a connector for connecting the cage to the plates. The fusion cage includes a superficial face, a deep face, superior and inferior saddle portions, and opposing cage ends. Each cage end defining a facet fusion surface sized and configured to respectively contact the opposing facet joints. The first and second fixation plate are sized and configured to extend along and in contact with the adjacent spinous processes. A method of implanting the device is provided. In another embodiment the device includes the fusion cage.

16 Claims, 13 Drawing Sheets

(56) References Cited

U.S. PATENT DOCUMENTS

| | | | |
|---|---|---|---|
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,280,444 B1 | 8/2001 | Zucherman et al. | |
| 6,312,431 B1 | 11/2001 | Asfora | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,626,944 B1 | 9/2003 | Taylor | |
| 6,652,527 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,761,720 B1 | 7/2004 | Senegas | |
| 6,796,983 B1 | 9/2004 | Zucherman et al. | |
| 6,902,566 B2 | 6/2005 | Zucherman et al. | |
| 6,946,000 B2 | 9/2005 | Senegas et al. | |
| 6,955,677 B2 * | 10/2005 | Dahners | A61B 17/8057 606/281 |
| 7,029,473 B2 | 4/2006 | Zucherman et al. | |
| 7,087,083 B2 | 8/2006 | Pasquet et al. | |
| 7,101,375 B2 | 9/2006 | Zucherman et al. | |
| 7,163,558 B2 | 1/2007 | Senegas et al. | |
| 7,189,234 B2 | 3/2007 | Zucherman et al. | |
| 7,201,751 B2 | 4/2007 | Zucherman et al. | |
| 7,238,204 B2 | 7/2007 | Le et al. | |
| 7,306,628 B2 | 12/2007 | Zucherman et al. | |
| 7,335,203 B2 | 2/2008 | Winslow et al. | |
| 7,473,268 B2 | 1/2009 | Zucherman et al. | |
| 7,476,251 B2 | 1/2009 | Zucherman et al. | |
| 7,481,839 B2 | 1/2009 | Zucherman et al. | |
| 8,048,120 B1 | 11/2011 | Fallin et al. | |
| 8,496,689 B2 | 7/2013 | Massoudi | |
| 2002/0091446 A1 | 7/2002 | Zucherman et al. | |
| 2002/0143331 A1 | 10/2002 | Zucherman et al. | |
| 2003/0040746 A1 * | 2/2003 | Mitchell | A61B 17/1606 623/17.11 |
| 2003/0045935 A1 * | 3/2003 | Angelucci et al. | 623/17.11 |
| 2003/0153915 A1 | 8/2003 | Nekozuka et al. | |
| 2003/0220643 A1 | 11/2003 | Ferree | |
| 2004/0097931 A1 | 5/2004 | Mitchell | |
| 2004/0153071 A1 | 8/2004 | Zucherman et al. | |
| 2004/0167520 A1 | 8/2004 | Zucherman et al. | |
| 2004/0193159 A1 | 9/2004 | Zucherman et al. | |
| 2004/0220568 A1 | 11/2004 | Zucherman et al. | |
| 2004/0249379 A1 | 12/2004 | Winslow et al. | |
| 2005/0010293 A1 | 1/2005 | Zucherman et al. | |
| 2005/0010298 A1 | 1/2005 | Zucherman et al. | |
| 2005/0075634 A1 | 4/2005 | Zucherman et al. | |
| 2005/0101955 A1 | 5/2005 | Zucherman et al. | |
| 2005/0143738 A1 | 6/2005 | Zucherman et al. | |
| 2005/0143827 A1 | 6/2005 | Globerman et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0209603 A1 | 9/2005 | Zucherman et al. | |
| 2005/0228383 A1 | 10/2005 | Zucherman et al. | |
| 2005/0228384 A1 | 10/2005 | Zucherman et al. | |
| 2005/0240182 A1 | 10/2005 | Zucherman et al. | |
| 2005/0245929 A1 | 11/2005 | Winslow et al. | |
| 2005/0245937 A1 | 11/2005 | Winslow | |
| 2005/0261768 A1 | 11/2005 | Trieu | |
| 2005/0288672 A1 | 12/2005 | Ferree | |
| 2006/0004447 A1 | 1/2006 | Mastrorio | |
| 2006/0015181 A1 | 1/2006 | Elberg | |
| 2006/0036258 A1 | 2/2006 | Zucherman et al. | |
| 2006/0036259 A1 | 2/2006 | Carl et al. | |
| 2006/0064166 A1 | 3/2006 | Zucherman et al. | |
| 2006/0084983 A1 | 4/2006 | Kim | |
| 2006/0084985 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0089654 A1 | 4/2006 | Lins et al. | |
| 2006/0089718 A1 | 4/2006 | Zucherman et al. | |
| 2006/0106381 A1 | 5/2006 | Ferree et al. | |
| 2006/0106397 A1 | 5/2006 | Lins | |
| 2006/0122620 A1 | 6/2006 | Kim | |
| 2006/0136060 A1 | 6/2006 | Taylor | |
| 2006/0149383 A1 | 7/2006 | Arnin et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0235521 A1 | 10/2006 | Zucherman et al. | |
| 2006/0241601 A1 | 10/2006 | Trautwein et al. | |
| 2006/0241610 A1 | 10/2006 | Lim et al. | |
| 2006/0064165 A1 | 11/2006 | Zucherman et al. | |
| 2006/0247623 A1 | 11/2006 | Anderson et al. | |
| 2006/0247634 A1 * | 11/2006 | Warner et al. | 606/61 |
| 2006/0247640 A1 | 11/2006 | Blackwell et al. | |
| 2006/0264938 A1 | 11/2006 | Zucherman et al. | |
| 2006/0264939 A1 | 11/2006 | Zucherman et al. | |
| 2006/0265066 A1 | 11/2006 | Zucherman et al. | |
| 2006/0265067 A1 | 11/2006 | Zucherman et al. | |
| 2006/0271049 A1 | 11/2006 | Zucherman et al. | |
| 2006/0271055 A1 | 11/2006 | Thramann | |
| 2006/0271194 A1 | 11/2006 | Zucherman et al. | |
| 2006/0293662 A1 * | 12/2006 | Boyer et al. | 606/61 |
| 2007/0005064 A1 | 1/2007 | Anderson et al. | |
| 2007/0010813 A1 | 1/2007 | Zucherman et al. | |
| 2007/0016303 A1 | 1/2007 | Jackson | |
| 2007/0032790 A1 | 2/2007 | Aschmann et al. | |
| 2007/0043361 A1 | 2/2007 | Malandain et al. | |
| 2007/0043362 A1 | 2/2007 | Malandain et al. | |
| 2007/0043363 A1 | 2/2007 | Malandain et al. | |
| 2007/0049934 A1 | 3/2007 | Edidin et al. | |
| 2007/0049935 A1 | 3/2007 | Edidin et al. | |
| 2007/0055237 A1 | 3/2007 | Edidin et al. | |
| 2007/0055246 A1 | 3/2007 | Zucherman et al. | |
| 2007/0073292 A1 | 3/2007 | Kohm et al. | |
| 2007/0093823 A1 | 4/2007 | Booth et al. | |
| 2007/0093825 A1 * | 4/2007 | Ferree et al. | 606/61 |
| 2007/0093828 A1 | 4/2007 | Abdou | |
| 2007/0093830 A1 | 4/2007 | Zucherman et al. | |
| 2007/0100340 A1 | 5/2007 | Lange et al. | |
| 2007/0106298 A1 | 5/2007 | Carli et al. | |
| 2007/0112354 A1 | 5/2007 | Iwasaki et al. | |
| 2007/0123861 A1 | 5/2007 | Dewey et al. | |
| 2007/0149972 A1 | 6/2007 | Nakajima et al. | |
| 2007/0161992 A1 | 7/2007 | Kwak et al. | |
| 2007/0161993 A1 | 7/2007 | Lowery et al. | |
| 2007/0162000 A1 | 7/2007 | Perkins | |
| 2007/0162005 A1 | 7/2007 | Peterson et al. | |
| 2007/0167945 A1 | 7/2007 | Lange et al. | |
| 2007/0173818 A1 * | 7/2007 | Hestad et al. | 606/61 |
| 2007/0173821 A1 | 7/2007 | Trieu | |
| 2007/0173823 A1 | 7/2007 | Dewey et al. | |
| 2007/0173832 A1 | 7/2007 | Tebbe et al. | |
| 2007/0185490 A1 | 8/2007 | Implicito | |
| 2007/0191837 A1 | 8/2007 | Trieu | |
| 2007/0191838 A1 | 8/2007 | Bruneau et al. | |
| 2007/0191847 A1 | 8/2007 | Arnin et al. | |
| 2007/0191947 A1 | 8/2007 | Arnin et al. | |
| 2007/0191948 A1 | 8/2007 | Arnin et al. | |
| 2007/0191949 A1 | 8/2007 | Arnin et al. | |
| 2007/0191950 A1 | 8/2007 | Arnin et al. | |
| 2007/0203490 A1 | 8/2007 | Zucherman et al. | |
| 2007/0203491 A1 | 8/2007 | Pasquet et al. | |
| 2007/0203493 A1 | 8/2007 | Zucherman et al. | |

(56) References Cited

U.S. PATENT DOCUMENTS

| | | |
|---|---|---|
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208347 A1 | 9/2007 | Zucherman et al. |
| 2007/0213724 A1 | 9/2007 | Arnin et al. |
| 2007/0213824 A1* | 9/2007 | Trieu ........................ 623/17.11 |
| 2007/0213829 A1 | 9/2007 | Le et al. |
| 2007/0219552 A1 | 9/2007 | Zucherman et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233083 A1 | 10/2007 | Abdou |
| 2007/0233088 A1 | 10/2007 | Edmond |
| 2007/0233096 A1 | 10/2007 | Garcia-Bengochea |
| 2007/0233098 A1 | 10/2007 | Mastrorio et al. |
| 2007/0233118 A1 | 10/2007 | Mclain |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0270823 A1 | 11/2007 | Trieu et al. |
| 2007/0270825 A1 | 11/2007 | Carls et al. |
| 2007/0270826 A1 | 11/2007 | Trieu et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0272259 A1 | 11/2007 | Allard et al. |
| 2007/0276368 A1 | 11/2007 | Trieu et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276381 A1 | 11/2007 | Butler et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2007/0282340 A1 | 12/2007 | Malandain |
| 2007/0282442 A1 | 12/2007 | Malandain et al. |
| 2007/0282443 A1 | 12/2007 | Globerman et al. |
| 2007/0288006 A1 | 12/2007 | Arnin et al. |
| 2007/0299526 A1 | 12/2007 | Malandain |
| 2008/0004706 A1 | 1/2008 | Arnin et al. |
| 2008/0009866 A1 | 1/2008 | Alamin et al. |
| 2008/0009947 A1 | 1/2008 | Arnin et al. |
| 2008/0009948 A1 | 1/2008 | Amin et al. |
| 2008/0015609 A1 | 1/2008 | Trautwein et al. |
| 2008/0015693 A1 | 1/2008 | Le Couedic |
| 2008/0015700 A1 | 1/2008 | Zucherman et al. |
| 2008/0021460 A1 | 1/2008 | Bruneau et al. |
| 2008/0021468 A1 | 1/2008 | Zucherman et al. |
| 2008/0021471 A1* | 1/2008 | Winslow et al. ................ 606/61 |
| 2008/0021472 A1 | 1/2008 | Winslow et al. |
| 2008/0021560 A1 | 1/2008 | Zucherman et al. |
| 2008/0021561 A1 | 1/2008 | Zucherman et al. |
| 2008/0027433 A1 | 1/2008 | Kohm et al. |
| 2008/0027434 A1 | 1/2008 | Zucherman et al. |
| 2008/0027435 A1 | 1/2008 | Zucherman et al. |
| 2008/0027438 A1 | 1/2008 | Abdou |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033552 A1 | 2/2008 | Lee et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039944 A1 | 2/2008 | Malandain et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0046089 A1 | 2/2008 | Zucherman et al. |
| 2008/0051785 A1 | 2/2008 | Zucherman et al. |
| 2008/0051891 A1 | 2/2008 | Malandain et al. |
| 2008/0051892 A1 | 2/2008 | Malandain et al. |
| 2008/0051893 A1 | 2/2008 | Malandain et al. |
| 2008/0051894 A1 | 2/2008 | Malandain et al. |
| 2008/0051895 A1 | 2/2008 | Malandain et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0051906 A1 | 2/2008 | Malandain et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058934 A1 | 3/2008 | Malandain et al. |
| 2008/0058935 A1 | 3/2008 | Malandain et al. |
| 2008/0058936 A1 | 3/2008 | Malandain et al. |
| 2008/0058937 A1 | 3/2008 | Malandain et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071376 A1 | 3/2008 | Kohm et al. |
| 2008/0071378 A1 | 3/2008 | Zucherman et al. |
| 2008/0071380 A1 | 3/2008 | Sweeney |
| 2008/0082118 A1 | 4/2008 | Edidin et al. |
| 2008/0082167 A1 | 4/2008 | Edidin et al. |
| 2008/0082172 A1 | 4/2008 | Jackson et al. |
| 2008/0086212 A1 | 4/2008 | Zucherman et al. |
| 2008/0108990 A1 | 5/2008 | Mitchell et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0132952 A1 | 6/2008 | Malandain et al. |
| 2008/0147190 A1 | 6/2008 | Dewey et al. |
| 2008/0147192 A1 | 6/2008 | Edidin et al. |
| 2008/0161818 A1 | 7/2008 | Kloss et al. |
| 2008/0161822 A1 | 7/2008 | Perez-Cruet |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177264 A1 | 7/2008 | Alamin et al. |
| 2008/0177271 A1 | 7/2008 | Yeh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0183210 A1 | 7/2008 | Zucherman et al. |
| 2008/0183211 A1 | 7/2008 | Lamborne et al. |
| 2008/0183218 A1* | 7/2008 | Mueller et al. ................ 606/280 |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234735 A1 | 9/2008 | Joshi |
| 2008/0234824 A1 | 9/2008 | Youssef et al. |
| 2008/0243250 A1 | 10/2008 | Seifert et al. |

(56) References Cited

U.S. PATENT DOCUMENTS

| | | |
|---|---|---|
| 2008/0249528 A1 | 10/2008 | Khalife |
| 2008/0255616 A1 | 10/2008 | Atkinson et al. |
| 2008/0255668 A1 | 10/2008 | Fallin et al. |
| 2008/0255669 A1 | 10/2008 | Fallin et al. |
| 2008/0262549 A1 | 10/2008 | Bennett et al. |
| 2008/0262617 A1 | 10/2008 | Froehlich et al. |
| 2008/0262619 A1 | 10/2008 | Ray |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2008/0287997 A1 | 11/2008 | Altarac et al. |
| 2008/0288072 A1 | 11/2008 | Kohm |
| 2008/0288075 A1 | 11/2008 | Zucherman et al. |
| 2008/0288078 A1 | 11/2008 | Kohm et al. |
| 2008/0294199 A1 | 11/2008 | Kohm et al. |
| 2008/0294200 A1 | 11/2008 | Kohm et al. |
| 2008/0294263 A1 | 11/2008 | Altarac et al. |
| 2008/0300686 A1 | 12/2008 | Khoo |
| 2008/0300687 A1 | 12/2008 | Lin et al. |
| 2008/0312741 A1 | 12/2008 | Lee et al. |
| 2008/0319487 A1 | 12/2008 | Fielding et al. |
| 2008/0319549 A1 | 12/2008 | Greenhalgh et al. |
| 2008/0319550 A1 | 12/2008 | Altarac et al. |
| 2009/0005819 A1 | 1/2009 | Ben-Mokhtar et al. |
| 2009/0005873 A1 | 1/2009 | Slivka et al. |
| 2009/0012528 A1 | 1/2009 | Aschmann et al. |
| 2009/0018658 A1 | 1/2009 | Garcia |
| 2009/0018662 A1 | 1/2009 | Pasquet et al. |
| 2009/0030523 A1 | 1/2009 | Taylor |
| 2009/0036925 A1 | 2/2009 | Sala et al. |
| 2009/0043342 A1 | 2/2009 | Freedland |
| 2009/0054931 A1 | 2/2009 | Metz-Stavenhagen |
| 2009/0054988 A1 | 2/2009 | Hess |
| 2009/0062915 A1 | 3/2009 | Kohm et al. |
| 2009/0264927 A1* | 10/2009 | Ginsberg et al. ............ 606/246 |
| 2010/0191287 A1 | 7/2010 | Bucci |
| 2011/0022090 A1 | 1/2011 | Gordon et al. |
| 2011/0144692 A1* | 6/2011 | Saladin et al. ............... 606/249 |
| 2011/0160772 A1* | 6/2011 | Arcenio et al. ............... 606/248 |
| 2012/0016418 A1* | 1/2012 | Chin et al. .................... 606/249 |
| 2012/0136392 A1* | 5/2012 | Keegan et al. ............... 606/249 |
| 2013/0123923 A1* | 5/2013 | Pavlov et al. ............ 623/17.16 |
| 2013/0317550 A1 | 11/2013 | Massoudi |

OTHER PUBLICATIONS

Copenheaver, Blaine R., PCT International Search Report, dated Jun. 28, 2012, pp. 1-8.

* cited by examiner

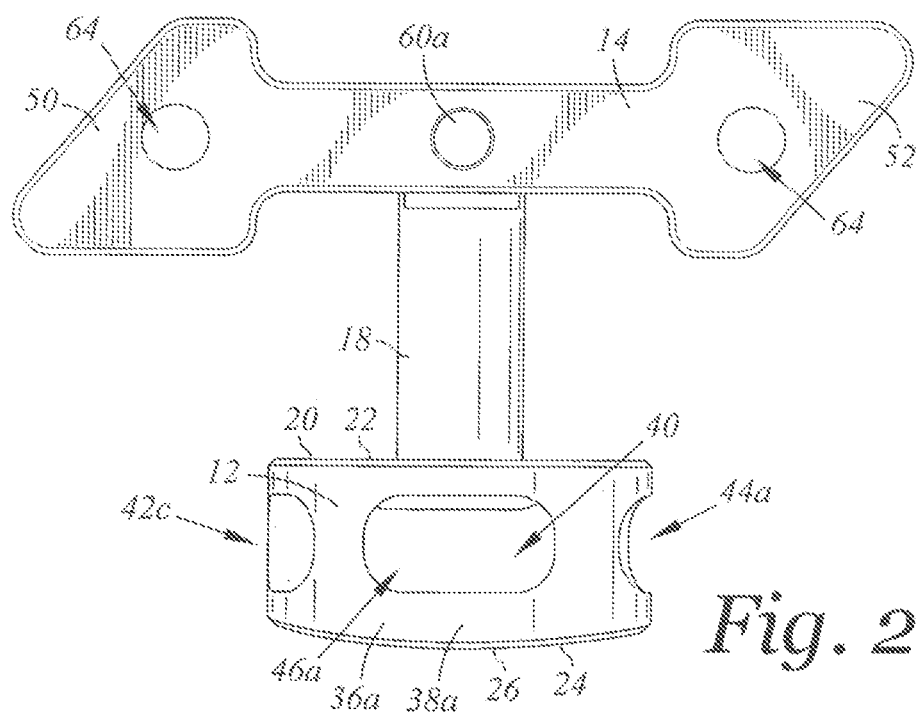
Fig. 2
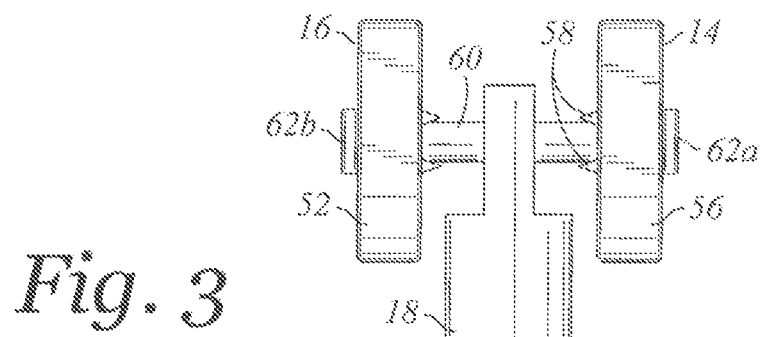
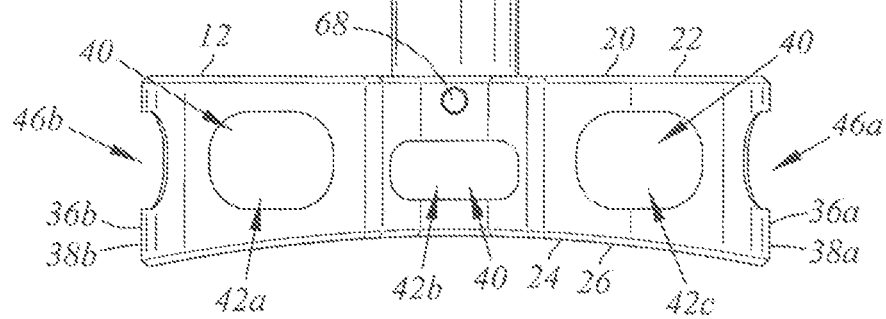
Fig. 3

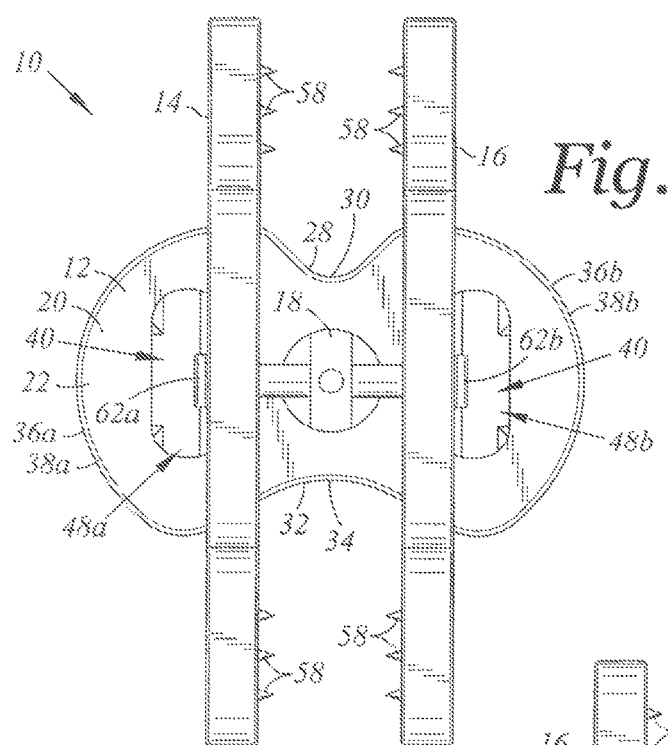
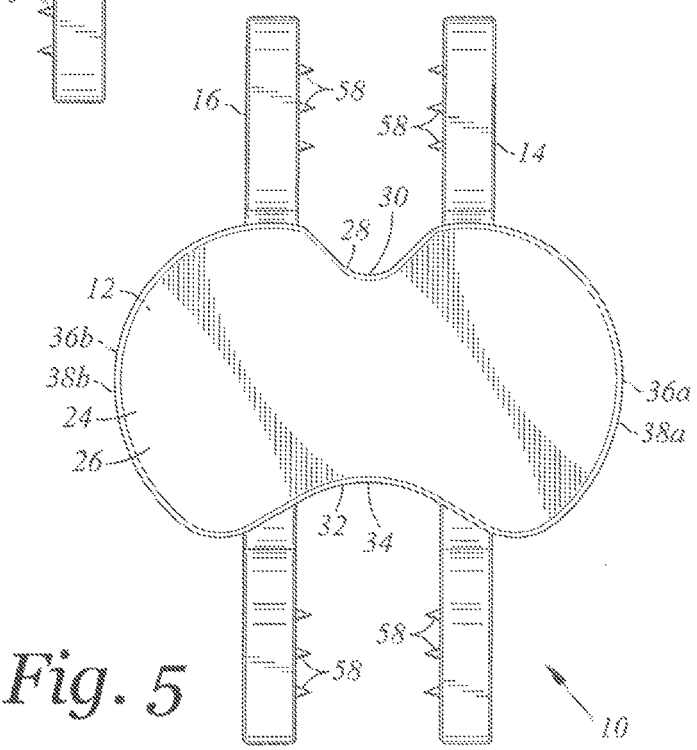

SPINAL IMPLANT DEVICE WITH FIXATION PLATES AND METHOD OF IMPLANTING

CROSS-REFERENCE TO RELATED APPLICATIONS

The present application is a continuation patent application of U.S. patent application Ser. No. 13/927,480, filed on Jun. 26, 2013, with is a divisional patent application of U.S. patent application Ser. No. 13/033,450, filed on Feb. 23, 2011, now U.S. Pat. No. 8,496,689, issued on Jul. 30, 2013, the entire contents of which are both incorporated herein by reference.

STATEMENT RE: FEDERALLY SPONSORED RESEARCH/DEVELOPMENT

Not Applicable

BACKGROUND

1. Technical Field

The present disclosure relates generally to spinal implant devices. More particularly, the present disclosure relates to spinal implant devices with a fusion cage and fixation plates and methods of implanting the same.

2. Related Art

There have been a myriad of spinal implant devices and techniques for treating spinal conditions that focus on fusion of the various levels of the lumbar spine. Moreover, a myriad of fixation devices and techniques have been implemented. Such fixation techniques range from use of peticle or facet screws with attached connecting rods to interspinous devices interacting with the spinous processes (such as spacers attaching the spinous processes with screw or bands). Implantation techniques may require multiple procedures which may be posterior and/or lateral in nature. Further, many devices require specialized surgical tools. Many attempts have been made to improve upon these devices and procedures to be minimally invasive, require a minimum number of procedures, and reduce recovery time. Such attempts have been met with varying degrees of success.

In view of the foregoing, there is a need in the art for an improved spinal implant device and method of implanting the same.

BRIEF SUMMARY

In accordance with one embodiment, a spinal implant device is provided for placement between adjacent spinous processes and adjacent a thecal sac. The spinous processes include a superior spinous process extending to a superior spinolaminar junction and an inferior spinous process extending to the inferior spinolaminar junction. The spinous processes are disposed about a pair of opposing facet joints. The spinal implant device includes a fusion cage, first and second fixation plates, and a connector. The fusion cage includes a superficial face defining an interspinous surface, and a deep face defining a thecal sac surface disposable adjacent the thecal sac. The fusion cage further includes a superior saddle portion defining a superior interlaminar fusion surface disposed between the superficial and deep faces. The superior saddle portion is sized and configured to receive the superior spinolaminar junction. The fusion cage further includes an inferior saddle portion defining an inferior interlaminar fusion surface disposed between the superficial and deep faces. The inferior saddle portion is sized and configured to receive the inferior spinolaminar junction. The fusion cage further includes opposing cage ends. Each cage end defines a facet fusion surface disposed between the superior and inferior interlaminar fusion surfaces. The facet fusion surfaces are sized and configured to respectively contact the opposing facet joints. The first and second fixation plates each have a superior end and an inferior end. The first and second fixation plates each are sized and configured to extend along the adjacent spinous processes with the superior ends disposed about and in contact with the superior spinous process and the inferior ends disposed about and in contact with the inferior spinous process. The connector extends from the superficial face and is connected to the first and second fixation plates.

The spinal implant device allows for simultaneous posterior minimally invasive neural decompression and fusion and allows for instrumentation at all levels of the lumbar spine extending to S1. Advantageously, the spinal implant device incorporates posterior interspinous and facet fusion concepts in a single device. Further, the use of the fixation plates facilitates fixation of the fusion cage in a single device. It is contemplated that it may be utilized in a single or multi level construct and be extended up to three levels in the L1 to S1 region of the spine. An aspect of the invention recognizes that the interspinous interlaminar space unique allows bone fusion of adjacent spinolaminar junctions and facet joints through a single surgical window using a single device.

It is contemplated that the spinal implant device may be implanted in through a minimally disruptive surgery. In this regard, muscle and ligaments attached to the transverse processes and facet joints need not be directly or substantially disturbed. The spinal implant device may be deployed with a midline exposure minimally invasive retractor based system or in standard minimally open fashion. It is contemplated that interlaminar exposure would provide the surgical window for neural decompression and spinolaminar decortications combined with medial partial bilateral facetectomies, which would provide the surface area necessary for fusion.

An aspect of the invention is that the spinal implant device facilitates synergistic and optimal interspinous fusion results far exceeding the potential of either interspinous or facet fusion devices alone or in combination. It is contemplated that the spinal implant device substantially reduces the operative time, perioperative morbidity and postoperative patient recovery in comparison to other prior devices and procedures whether alone or in combination with each other. Further, the design allows for interspinous and facet fusion without the need for pedicle or facet screws which may result in iatrogenic destabilization of the motion segment. Moreover, the design avoids transverse process fusion, which is contemplated to be highly invasive.

In accordance with various embodiments, the fusion cage may include a cage recess. The superior interlaminar fusion surface may include a superior opening extending to the cage recess, and the inferior interlaminar fusion surface may include an inferior opening extending to the cage recess. In addition, each of the facet fusion surfaces may include a facet opening extending to the cage recess. Further, the interspinous surface may include interspinous openings therein extending to the cage recess. In an embodiment, the superior and inferior interlaminar fusion surfaces are concave shaped, the facet fusion surfaces are convex shaped, the interspinous surface is generally planar, and the thecal sac surface is concave. The thecal sac surface may be a continuously smooth surface.

The connector may be connected to the first and second fixation plates with the connector between the first and second fixation plates. The connector may be pivotably connected to the first and second fixation plates, such as through the use of a pin. The fixation plates may be configured to pivot in unison with regard to the connector. The first and second fixation plates may each include teeth for respectively engaging the spinous processes. The connector may be connected to the first and second fixation plates with a fastener sized and configured to compress the first and second fixation plates against the spinous processes. Each of the first and second fixation plates has a superior end and an inferior end, and the fixation plates each may be sized and configured to extend along the adjacent spinous processes with the superior ends disposed about and in contact with the superior spinous process and the inferior ends disposed about and in contact with the inferior spinous process. The superior ends and the inferior ends may each include a screw hole, and the spinal implant device further may include a first screw sized and configured to extend through the screw holes of the superior ends with the superior ends disposed about the superior spinous process. The spinal implant device may further include a second screw sized and configured to extend through the screw holes of the inferior ends with the inferior ends disposed about the inferior spinous process. The first and second screws may be lag screws. In this regard, the screw hole of the superior end of the first fixation plate may be threaded and sized and configured to threadedly engage the first screw, and the screw hole of the inferior end of the first fixation plate may be threaded and sized and configured to threadedly engage the second screw.

In another embodiment, the connector is rigidly connected to the superficial face. The connector may be integrated with the fusion cage with the connector and the fusion cage formed of a common material having material continuity. In another embodiment, the connector defines a longitudinal axis and the connector is rotatably connected to the cage with respect to rotation about the longitudinal axis. Further, the connector may be pivotably connected to the cage with respect to pivoting about an axis other than the longitudinal axis.

According to another embodiment, there is provided a method of implanting a spinal implant device for placement between adjacent spinous processes and adjacent a thecal sac. The spinous processes include a superior spinous process extending to a superior spinolaminar junction and an inferior spinous process extending to the inferior spinolaminar junction. The spinous processes are disposed about a pair of opposing facet joints. The method includes removing a portion of the superior spinolaminar junction. The method further includes removing a portion of each of the facet joints. The method further includes providing the spinal implant device including a fusion cage, first and second fixation plates and a connector extending between the fusion cage and the first and second fusion plates. The fusion cage has a superior saddle portion, an inferior saddle portion and opposing cage ends. The method further includes positioning the fusion cage between the spinous processes with the superior saddle portion receiving the superior spinolaminar junction where the portion of the superior spinolaminar junction has been removed, and the inferior saddle portion receiving the inferior spinolaminar junction. The opposing cage ends are respectively contacting the opposing facet joints where the portion of each of the facet joints has been removed. The method further includes attaching the first and second fixation plates to the adjacent spinous processes with the spinous processes disposed between the fixation plates. The method may further include selecting the spinal implant device from an array of spinal implant devices each with a fusion cage, but with varying fusion cage dimensions.

The cage may include a cage recess. The method may further include exposing the cage recess to the superior spinolaminar junction. The method may further include exposing the cage recess to the inferior spinolaminar junction. A boney fusion mass may be disposed within the cage recess. The method may further include exposing the boney fusion mass to the superior spinolaminar junction. The method may further include exposing the boney fusion mass to the inferior spinolaminar junction. The method may further include removing a portion of the superior spinous process. The method may further include removing a portion of the inferior spinolaminar junction. The superior spinolaminar junction extends to a lamina and the fusion cage includes a superficial face defining an interspinous surface and a deep face defining a thecal sac surface. The method may further include positioning the fusion cage with the interspinious surface generally aligned with the lamina and the thecal sac surface aligned with the thecal sac. Further a superior spinolaminar junction extends to a superior lamina and the inferior spinolaminar junction extends to an inferior lamina. The method may further include disposing a boney fusion mass in contact with the superior lamina and the inferior lamina across and in contact with the fusion cage. The fusion cage may include a superficial face and defining an interspinous surface and an opposing deep face. The interspinous surface may include interspinous openings therein extending to the cage recess, and the interspinous openings are exposed to the boney fusion mass. The method may further include disposing a boney fusion mass in contact with the superior lamina and the inferior lamina across and in contact with the boney fusion mass within the fusion cage.

The method may include using a fastener to compress the first and second fixation plates to the adjacent spinous processes with the spinous processes disposed between the fixation plates. The fastener may be disposed between the spinous processes. The first and second fixation plates may include teeth, and the method may further include positioning the teeth respectively against the spinous processes. The method may further include attaching the fixation plates to the spinous processes with screws. The method may further include inserting a screw through the first fixation plate, through the spinous process and through the second fixation plate. The method may further include inserting a lag screw through the first fixation plate, and through the superior spinous process, and screwing the screw into the second fixation plate. The method may further include drilling a hole through the superior spinous process. The method may include providing a drill guide engaged with the first fixation plate, and inserting a drill bit through the drill guide through the first fixation plate and into the superior spinous process.

In accordance with another embodiment, a spinal implant device is provided for placement between adjacent spinous processes and adjacent a thecal sac. The spinous processes include a superior spinous process extending to a superior spinolaminar junction and an inferior spinous process extending to the inferior spinolaminar junction. The spinous processes are disposed about a pair of opposing facet joints. The spinal implant device includes a fusion cage. The fusion cage includes a superficial face defining an interspinous surface, and a deep face defining a thecal sac surface disposable adjacent the thecal sac. The fusion cage further includes a superior saddle portion defining a superior interlaminar fusion surface disposed between the superficial and deep faces. The superior saddle portion is sized and configured to receive the superior spinolaminar junction. The fusion cage further includes an inferior saddle portion defining an inferior interlaminar fusion surface disposed between the superficial and deep faces. The inferior saddle portion is sized and configured to receive the inferior spinolaminar junction. The fusion cage further includes opposing cage ends. Each cage end defines a facet fusion surface disposed between the superior and inferior interlaminar fusion surfaces. The facet fusion surfaces are sized and configured to respectively contact the opposing facet joints. The first and second fixation plates each have a superior end and an inferior end.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 2 is a side view of the spinal implant device of FIG. 1;

FIG. 3 is an end view of the spinal implant device of FIG. 1;

FIG. 4 is a top view of the spinal implant device of FIG. 1;

FIG. 5 is a bottom view of the spinal implant device of FIG. 1;

FIG. 8a is a side view illustrating the L4 and L5 vertebrae of FIG. 6a;

FIG. 10b is an assembled view of the portion of the spinal implant device of FIG. 10a;

FIG. 13b is a reverse side view of a spinal implant device of FIG. 13a;

Common reference numerals are used throughout the drawings and the detailed description to indicate the same elements.

DETAILED DESCRIPTION

The detailed description set forth below in connection with the appended drawings is intended as a description of certain embodiments of the present disclosure, and is not intended to represent the only forms that may be developed or utilized. The description sets forth the various functions in connection with the illustrated embodiments, but it is to be understood, however, that the same or equivalent functions may be accomplished by different embodiments that are also intended to be encompassed within the scope of the present disclosure. It is further understood that the use of relational terms such as top and bottom, first and second, and the like are used solely to distinguish one entity from another without necessarily requiring or implying any actual such relationship or order between such entities.

Figure 1:
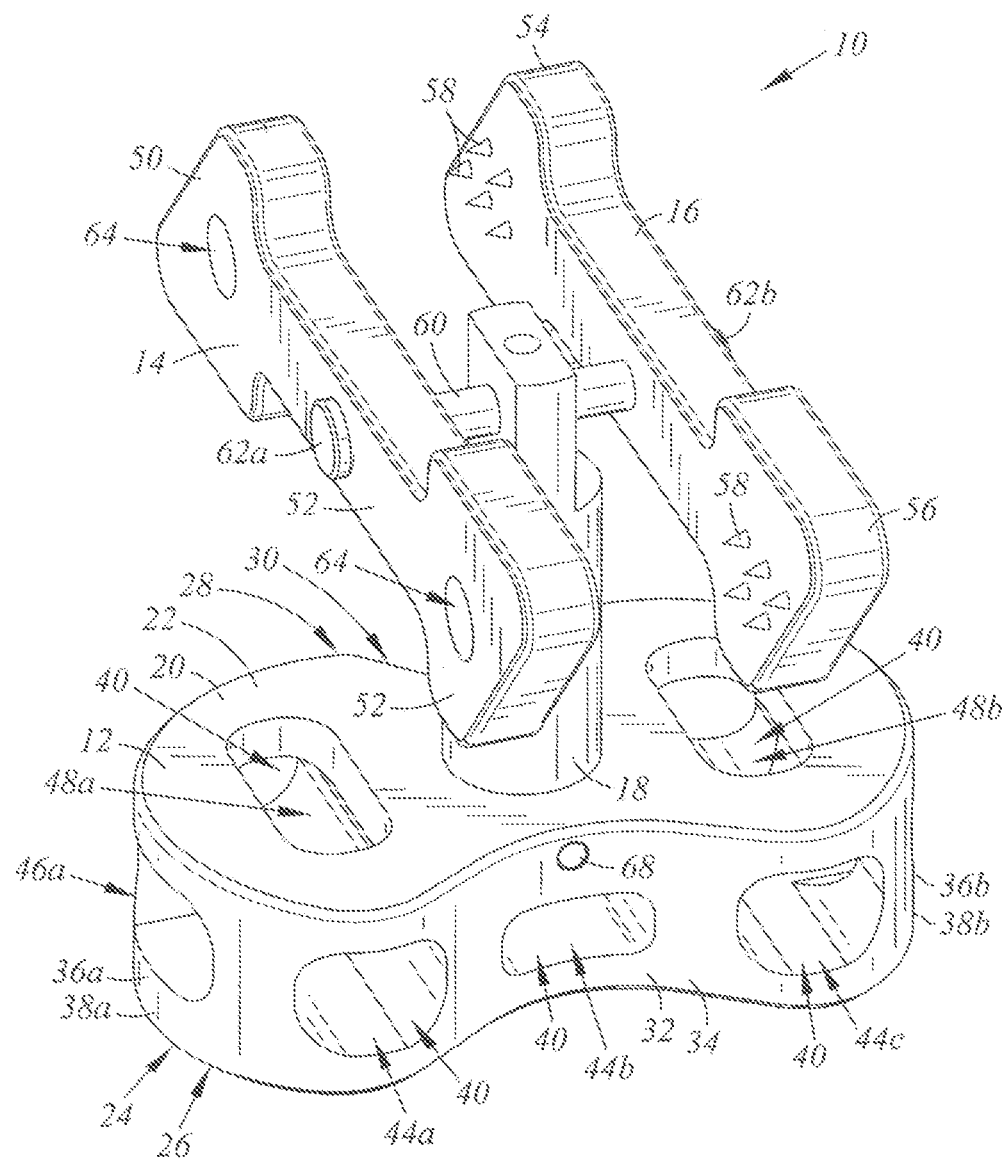
FIG. 1 is a perspective view of a spinal implant device according to an embodiment of the invention.

Referring now to FIG. 1, there is depicted a perspective view of a spinal implant device 10 according to an embodiment of the invention. FIG. 2 is a side view of the spinal implant device 10, FIG. 3 is an end view of the spinal implant device 10, FIG. 4 is a top view of the spinal implant device 10, and FIG. 5 is a bottom view of the spinal implant device 10.

Figure 6A:
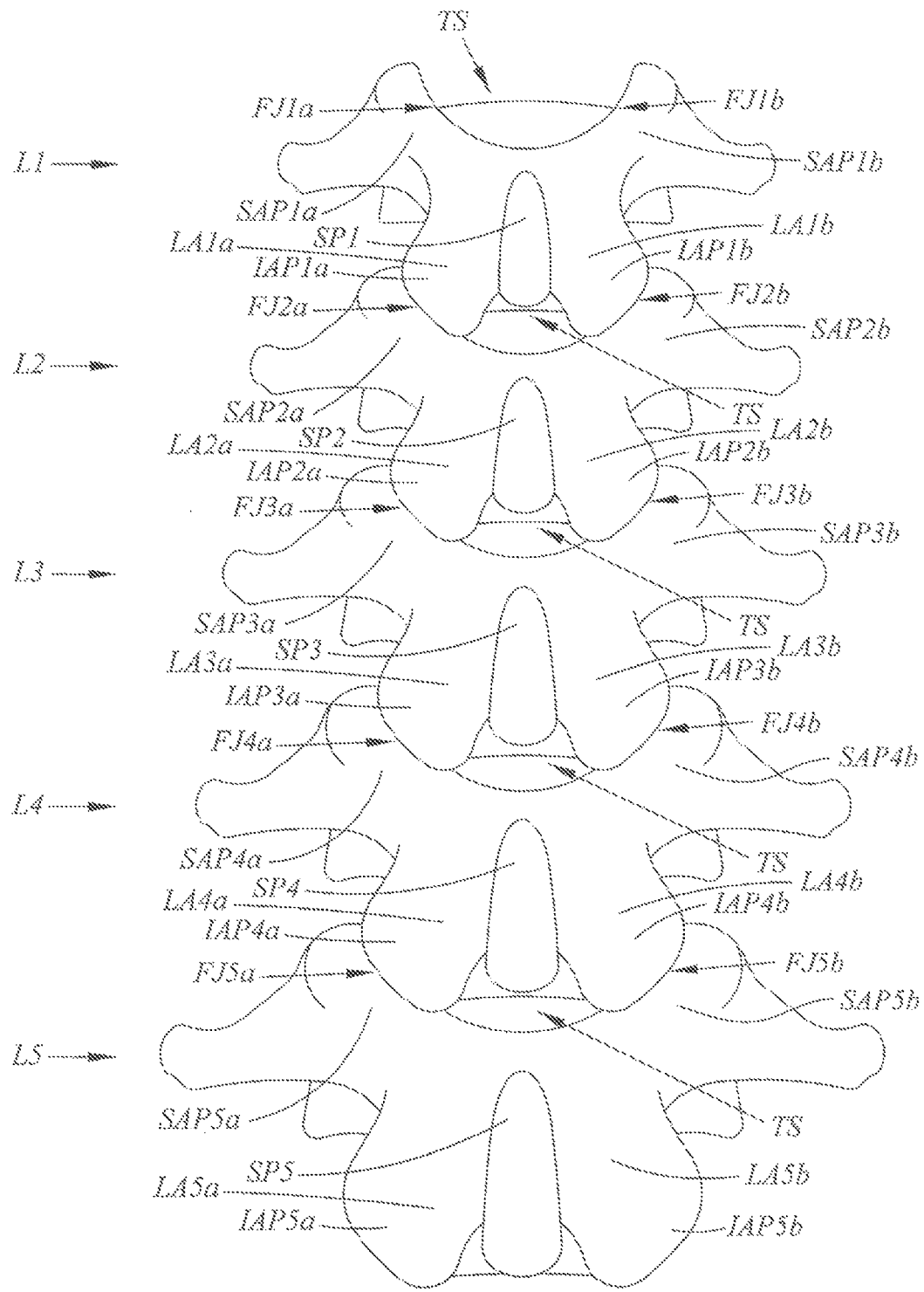
FIG. 6a is a posterior view illustrating the lumbar region of the spine taken along the sagittal plane.

FIG. 6a is a posterior view illustrating the lumbar region of the spine taken along the sagittal plane. The lumbar spine includes a series of stacked vertebrae (L1-5). Each vertebra includes a spinous process (SP1-SP5), lamina (LA1-5 a, b) and a pair of facet joints (FJ1-FJ5 a, b). The facet joint (also referred to as the zygapophysial joint or zygapophyseal) is a synovial joint between the superior articular process (SAP1-5 a, b) of one vertebra and the inferior articular process (IAP1-5 a, b) of the vertebra directly above it. The lamina (LA1-5 a, b) is the flattened posterior part of the vertebral arch from which the spinous process (SP1-5) extends. Between the lamina (LA1-5 a, b) and the spinous process (SP1-5) is the spinolaminar junction.

Figure 6B:
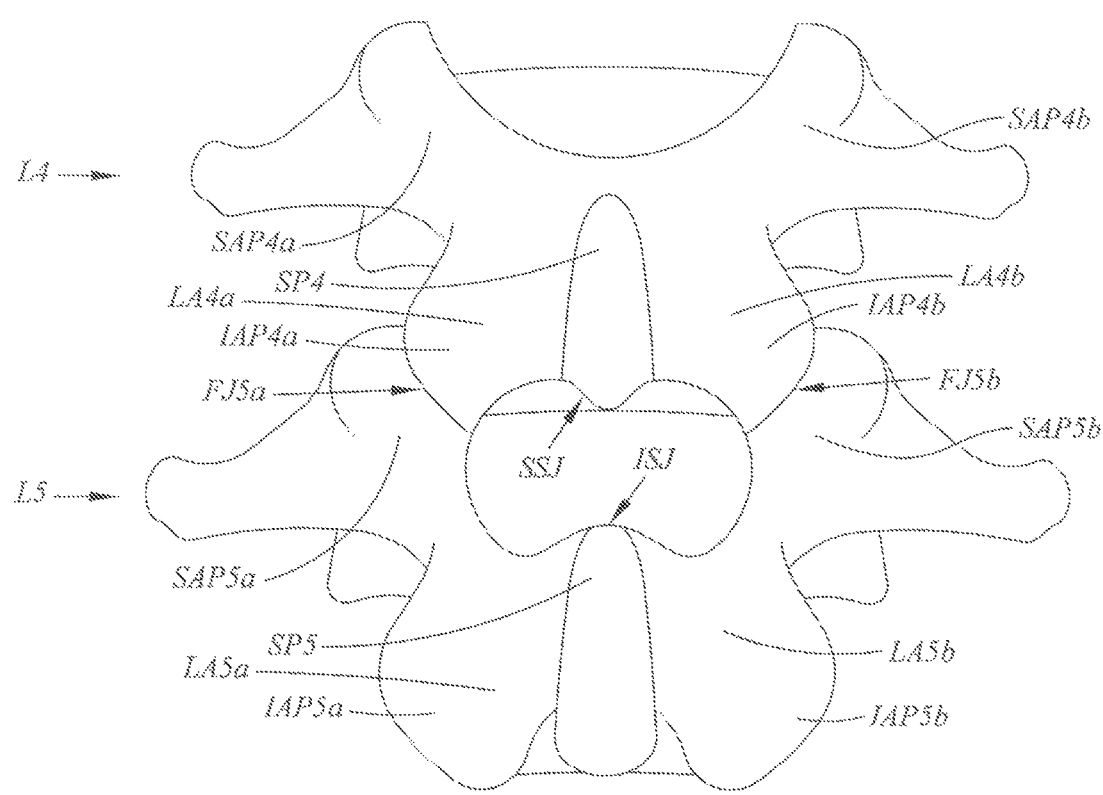
FIG. 6b is a posterior view illustrating two vertebrae L4 and L5 of the lumbar region of the spine of FIG. 6a with portions removed in preparation of receiving the spinal implant device.
Figure 7A:
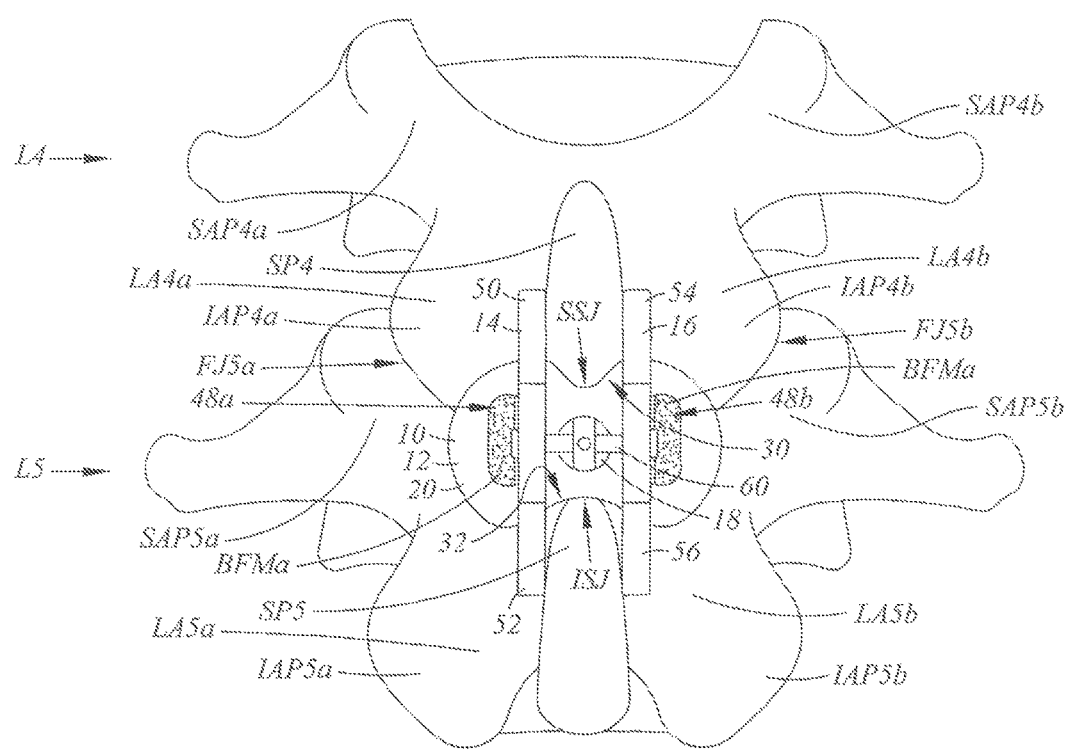
FIG. 7a is the posterior view illustrating the two vertebrae L4 and L5 of the lumbar region of the spine of FIG. 6b with the spinal implant device installed with the spinal implant device including a boney mass inside a fusion cage.
Figure 8A:
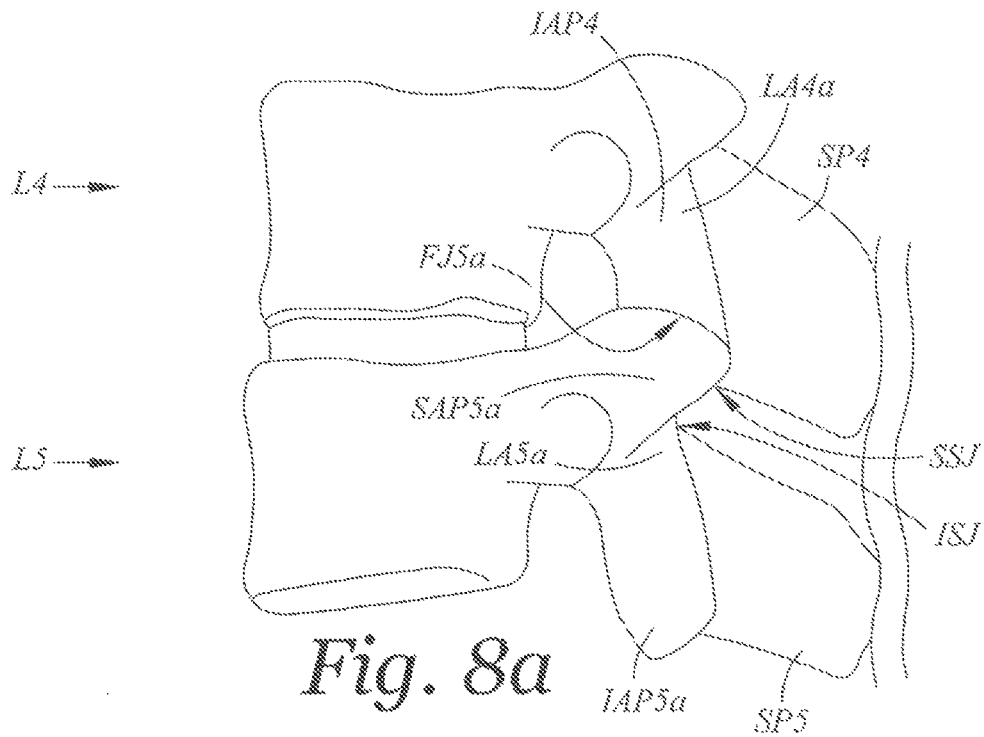
Figure 8B:
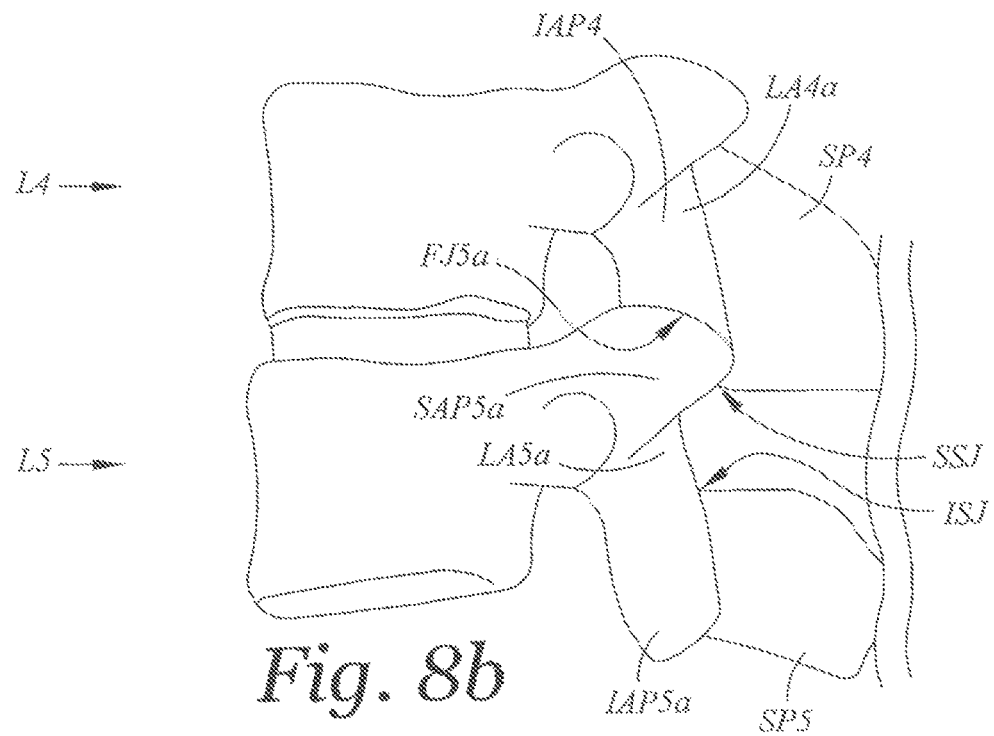
FIG. 8b is the side view illustrating the L4 and L5 vertebrae of FIG. 8a with portions of the spine having been removed in preparation of receiving the spinal implant device.
Figure 9A:
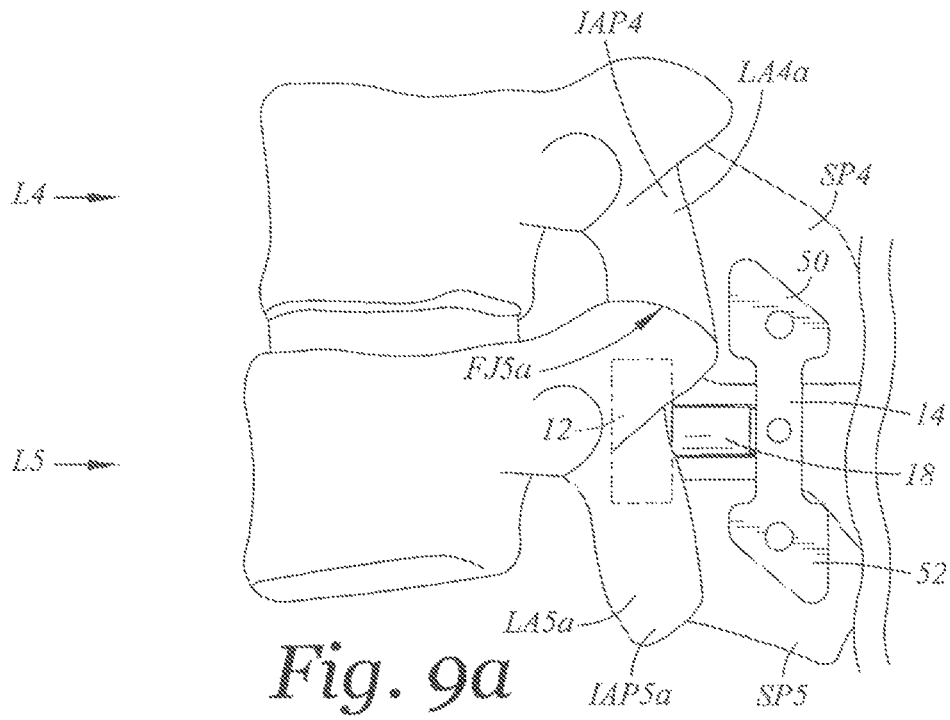
FIG. 9a is the side view illustrating the L4 and L5 vertebrae of FIG. 8b with the spinal implant device installed (portions of which shown in phantom)

The spinal implant device 10 is for use with installation within a spine. In this regard, referring additionally to FIG. 6a there is provided a posterior view illustrating the lumbar region of the spine taken along the sagittal plane. FIG. 6b is a posterior view illustrating the two lowermost vertebrae L4 and L5 of the lumbar region of the spine of FIG. 6a, with portions having been removed in preparation of receiving the spinal implant device 10. FIG. 7a is the posterior view illustrating the two vertebrae (L4, L5) of FIG. 6b with the spinal implant device 10 installed. Further, FIG. 8a is a side view illustrating the vertebrae (L4, L5) of FIG. 6a, and FIG. 8b is the side view illustrating the vertebrae (L4, L5) of FIG. 8a with portions having been removed in preparation of receiving the spinal implant device 10. FIG. 9*a* is the side view illustrating the vertebrae (L4, L5) vertebrae of FIG. 8*b* with the spinal implant device 10 installed (portions of which shown in phantom).

In accordance with one embodiment, a spinal implant device 10 is provided for placement between adjacent spinous processes and adjacent a thecal sac. For example, the spinal implant device 10 may be installed between the two vertebrae (such as L4 and L5). As used herein in the context of installation of the spinal implant device 10 between two vertebrae (such as L4 and L5), the term superior refers to that skeletal structure anatomically positioned relatively above and the terms inferior refers to that skeletal structure anatomically positioned below. In this regard, for example, the spinal implant device 10 may be installed between the vertebrae (L4, L5). The adjacent spinous processes would be the SP4 and SP5 with the spinous processes (SP4) being referred to the superior spinous process and the spinous process (SP5) being referred to the inferior spinous process.

As such, in the example installation, the spinous processes include a superior spinous process SP4 and an inferior spinous process SP5. As best viewed in FIGS. 6*b* and 7*a*, the superior spinous process (SP4) extends to a superior spinolaminar junction (SSJ) and an inferior spinous process (SP5) extends to the inferior spinolaminar junction (IAJ). The spinous processes (SP4, SP5) are disposed about a pair of opposing facet joints (FJ5a, FJ5b). The spinal implant device 10 includes a fusion cage 12, first and second fixation plates 14, 16, and a connector 18. The fusion cage 12 includes a superficial face 20 defining an interspinous surface 22, and a deep face 24 defining a thecal sac surface 26 disposable adjacent the thecal sac (TS). The fusion cage 12 further includes a superior saddle portion 28 defining a superior interlaminar fusion surface 30 disposed between the superficial and deep faces 20, 24. The superior saddle portion 28 is sized and configured to receive the superior spinolaminar junction (SSJ). The fusion cage 12 further includes an inferior saddle portion 32 defining an inferior interlaminar fusion surface 34 disposed between the superficial and deep faces 20, 22. The inferior saddle portion 32 is sized and configured to receive the inferior spinolaminar junction (ISJ). The fusion cage 12 further includes opposing cage ends 36*a-b*. Each cage end 36*a-b* respectively defines a facet fusion surface 38*a-b* disposed between the superior and inferior interlaminar fusion surfaces 30, 34. The facet fusion surfaces 38*a-b* are sized and configured to respectively contact the opposing facet joints (FJ5a-b). The first and second fixation plates 14, 16 each respectively have a superior end 50, 54 and an inferior end 52, 54. The first and second fixation plates 14, 16 each are sized and configured to extend along the adjacent spinous processes (SP4, SP5) with the superior ends 50, 52 disposed about and in contact with the superior spinous process (SP4) and the inferior ends 52, 56 disposed about and in contact with the inferior spinous process (SP5). The connector 18 extends from the superficial face 20 and is connected to the first and second fixation plates 14, 16.

The spinal implant device 10 allows for simultaneous posterior minimally invasive neural decompression and fusion and allows for instrumentation at all levels of the lumbar spine extending to S1. Advantageously, the spinal implant device 10 incorporates posterior interspinous and facet fusion concepts in a single device. Further, the use of the fixation plates 14, 16 facilitates fixation of the fusion cage 12 in a single device. It is contemplated that it can be utilized in a single or multi level construct and be extended up to three levels in the L1 to S1 region of the spine. An aspect of the invention recognizes that the interspinous interlaminar space unique allows bone fusion of adjacent spinolaminar junctions and facet joints through a single surgical window using a single device.

It is contemplated that the spinal implant device 10 may be implanted in through a minimally disruptive surgery. In this regard, muscle and ligaments attached to the transverse processes and facet joints (FJ1-5 a-b) need not be directly or substantially disturbed. The spinal implant device may be deployed with a midline exposure minimally invasive retractor based system or in standard minimally open fashion. It is contemplated that interlaminar exposure would provide the surgical window for neural decompression and spinolaminar decortications combined with medial partial bilateral facetectomies would provide the surface area necessary for fusion.

An aspect of the invention is that the spinal implant device 10 facilitates synergistic and optimal interspinous fusion results, which far exceeds the potential of either interspinous or facet fusion devices alone or in combination. It is contemplated that the spinal implant device 10 substantially reduces the operative time, perioperative morbidity and postoperative patient recovery in comparison to other prior devices and procedures whether alone or in combination with each other. Further, the design allows for interspinous and facet fusion without the need for pedicle or facet screws which may result in iatrogenic destabilization of the motion segment. Moreover, the design avoids transverse process fusion which is contemplated to be highly invasive.

In accordance with various embodiments, the fusion cage 12 may include a cage recess 40. In the embodiment depicted in FIGS. 1-5, the cage recess 40 collectively takes the form of three separate recesses. It is contemplated that the cage recess 40 may be of the form other than three recesses, such as a single recess or a multitude of recesses. The superior interlaminar fusion surface 30 may include a superior opening 42*b* extending to the cage recess 40. The inferior interlaminar fusion surface may respectively include an inferior opening 44*a*, *b* extending to the cage recess 40. In addition, each of the facet fusion surfaces 38*a*, *b* may respectively include a facet opening 46*a*, *b* extending to the cage recess 40. As will be discussed further below, the cage recess 40 may be packed with a boney fusion mass (actual and/or artificial) to facilitate fusion between the fusion cage 12 and the adjacent vertebrae (L4, L5). The various openings (the superior opening 42*b*, the inferior opening 44*b*, and the facet openings 46*a-b*, and the interspinous openings 48*a-b*) facilitate direct access to the adjacent vertebrae (L4, L5) for fusion at such locations of exposure. Further, the interspinous surface 22 may include interspinous openings 48*a-b* therein extending to the cage recess 40. As further discussed below, boney fusion mass (actual and/or artificial) may be provided across the interspinous surface 22 to facilitate fusion. It is contemplated the fusion cage 12 may include more or less openings than as depicted in the present embodiment. In this regard, the fusion cage 12 may include portions that are formed of a honeycomb material or other porosity to facilitate fusion.

In an embodiment, the superior and inferior interlaminar fusion surfaces 30, 34 may be concave shaped. Such shape is contemplated to facilitate the superior saddle portion 28 to receive the superior spinolaminar junction (SSJ) and the inferior saddle portion 32 to receive the inferior spinolaminar junction (ISJ). The inferior interlaminar fusion surface 34 may be defined by an arc radius larger than an art radius of the superior interlaminar fusion surface 30 to accommodate the relatively larger structure of the inferior spinolaminar junction (ISJ).

Further, the facet fusion surfaces 38a, b may be convex shaped. In this respect, the embodiment depicted of the fusion cage is generally bean shaped or double oval shaped. Other shapes of the fusion cage 12 are contemplated; however, this particular configuration may be desirable as it strikes a balance between fusion potential and invasiveness with regard to the implantation procedure.

In addition, the interspinous surface 22 may generally planar, although other shapes are contemplated. The thecal sac surface 26 may be concave (as best seen in the end view of FIG. 3). In this regard the thecal sac surface 26 may be formed to re-create the roof of the spinal canal where portions are removed during the spinal implant device installation procedure. Further, the thecal sac surface 26 may be a continuously smooth surface. This regard fusion with the thecal sac (TS) may be mitigated.

The connector 18 may be connected to the first and second fixation plates 14, 16 with the connector 18 between the first and second fixation plates 14, 16. The connector 18 may be pivotably connected to the first and second fixation plates 14, 16. In this regard, the connector 18 may be connected to the first and second fixation plates with a pin 60. In the embodiment depicted, the pin 60 has a round cross section. Each of the first and second fixation plates 14, 16 may independently rotate about the pin 60. In addition, the pin 60 may rotate with respect to the connector 18. The length of the pin 60 may facilitate an ease of attachment and positioning of the first and second fixation plates 14, 16 with regard to the superior and inferior spinous processes (SP4, SP5). In this embodiment, the pin 60 may include end caps 62a, b. The end caps 62a, b may be press fit onto the pin 60 or material of the pin 60 may be deformed so as to form the end caps 62a-b after installation of the pin 60 with the connector 18 and the first and second fixation plates 14, 16 on the pin 60. It is contemplated that other arrangements for attaching the first and second fixation plates 14, 16 may be implemented, such as use of fasteners in lieu of the pin 60 as discussed below as well as any of those which are well known to one of ordinary skill in the art. In addition, components may be integrated with one or both of the fixation plates 14, 16. In this regard an end of the pin 60 could be modified to be integrated with one of the first or second fixation plates 14, 16.

The first and second fixation plates may each include teeth 58 for respectively engaging the spinous processes (SP4, SP5). The shape, number and sizing of the teeth 58 may vary depending upon such factors as material selection of the teeth 58 themselves and whether any other means of attaching the first and second fixation plates 14, 16 are utilized (such as a fastener to provide a compressive force of the first and second fixation plates 14, 16 to the spinous processes (SP4, SP5)). As mentioned above, the first and second fixation plates 14, 16 each are sized and configured to extend along the adjacent spinous processes (SP4, SP5) with the superior ends 50, 52 disposed about and in contact with the superior spinous process (SP4) and the inferior ends 52, 56 disposed about and in contact with the inferior spinous process (SP5). In this regard, the teeth 58 may be disposed at each of the superior ends, 50, 52 and the inferior ends 52, 56 at such locations where the first and second fixation plates 14, 16 are intended to contact the spinous processes (SP4, SP5).

The first and second fixation plates 14, 16 may include indexing features 64. The indexing features 64 may take the form of a simple dimple depression such as depicted in the embodiment. The indexing features 64 may be used as a gripping location such as for use with forceps during the installation procedure of the spinal implant device 10. Additionally, such gripping may be particularly useful when applying a compressive force against the first and second fixation plates 14, 16 as to bite the teeth 58 into the spinous processes (SP4, SP5). The design of the number, size and shape of the indexing features 64 may be adjusted depending upon the needs of the particular surgical instrumentation utilized.

The first and second fixation plates 14, 16 include the superior ends 50, 54 and the inferior ends 52, 56 that are tapered. Such tapering is contemplated to allow for similarly constructed spinal implant devices 10 to have their first and second fixation plates 14, 16 about each other where the spinal implant devices 10 are being deployed in a manner that shares a common spinous process (i.e., installations at adjacent levels).

The connector 18 may be rigidly connected to the superficial face 20. In the embodiment depicted, a pin insert 68 may be positioned in the fixation cage 12. Though not depicted, the pin insert 68 is engaged with the lower end of the connector 18 for rigidly securing the connector 18 to the fixation cage 12 and therefore the superficial face 20 from which it extends. The pin insert 68 may be provided during or after the fabrication process of the fusion cage 12. It is also contemplated that the connector 18 may be integrated with the fusion cage 12 with the connector 18 and the fusion cage 12 being formed of a common material having material continuity.

Suitable implant materials for the spinal implant device 10 may be chosen from those which are well known to one of ordinary skill in the art. In some embodiments, all components of the spinal implant device 10 may be of a same material or a combination of differing materials. It is contemplated that medical grade metals may be utilized, such as titanium, stainless steel, cobalt chrome, and alloys thereof. In this regard, other suitable materials include certain medical grade polymers. A group of biocompatible polymer is the polyaryl ester ketones which have several members including polyetheretherketone (PEEK) and polyetherketoneketone (PEKK). In an embodiment, the fusion cage 12 may be formed of PEEK and the connector 18 and the fixation plates 14, 16 may be formed of titanium. The use of titanium may be particularly desirable for the fixation plates 14, 16 due to the strength characteristics with regard to the formation of the teeth 58. While PEEK may be a desirable material selection for the fusion cage 12 as opposed to a relatively harder material like a metal which may compress and deform adjacent bone structures. In another embodiment, the fusion cage 12, connector 18 and the fixation plates 14, 16 may all be formed of PEEK. This may be desirable as this would be an all non-metal option.

According to another embodiment, there is provided a method of implanting the spinal implant device 10 for placement between adjacent spinous processes (such as between SP4 and SP5) and adjacent the thecal sac (TS). Referring now to FIG. 6b there is depicted a posterior view illustrating two vertebrae L4 and L5 of the lumbar region of the spine of FIG. 6a with portions removed in preparation of receiving the spinal implant device 10. FIG. 8b is the side view illustrating the L4 and L5 vertebrae of FIG. 8a with portions of the spine having been removed in preparation for receiving the spinal implant device 10. The method includes removing a portion of the superior spinolaminar junction (SSJ). The method further includes removing a portion of each of the facet joints (FJ5a-b). Having created a minimum surgical window, the method further includes providing the spinal implant device 10 such as described above and in additional embodiments below.

Referring now to FIG. 7*a* is the posterior view illustrating the two vertebrae L4 and L5 of the lumbar region of the spine of FIG. 6*b* with the spinal implant device 10 installed. FIG. 9*a* is the side view illustrating the L4 and L5 vertebrae of FIG. 8*b* with the spinal implant device 10 installed. The method further includes positioning the fusion cage 12 between the spinous processes (SP4, SP5) with the superior saddle portion 28 receiving the superior spinolaminar junction (SSJ) where the portion of the superior spinolaminar junction (SSJ) has been removed, and the inferior saddle portion 32 receiving the inferior spinolaminar junction (ISJ). The opposing cage ends 36*a*-*b* are respectively contacting the opposing facet joints (FJ5a, b) where the portion of each of the facet joints (FJ5a, b) has been removed.

The method further includes attaching the first and second fixation plates 14, 16 to the adjacent spinous processes (SP4, SP5) with the spinous processes (SP4, SP5) disposed between the first and second fixation plates 14, 16. In this regard, the method may further include positioning the teeth 58 respectively against the spinous processes (SP4, SP5).

In further detail, according to various embodiments of the method of the present invention, in creating the surgical window in preparation for the installation of the spinal implant device 10, the method may include removal of the posterior interspinous ligament and the ligamentum flavum inside the spinal canal. The method may further include removing a portion of the superior spinous process (SP4), such as is depicted in FIGS. 6*b* and 8*b*. In addition, the method may further include removing a portion of the inferior spinolaminar junction (ISJ), as is depicted in FIG. 8*b*.

It is contemplated that the surgeon is provided with an array of spinal implant devices 10 having differing sized components. In particular, there may be provided various spinal implant devices 10 each with a fusion cage 12, but with varying fusion cage dimensions. For example, the length of the fusion cage 12 as measured between the cage ends 36*a*, *b* (peak to peak) may be provided in multiple sizes, such as 4 cm., 6 cm. and 8 cm. (small, medium and large). It is contemplated that the surgeon may significantly control the proper size required by the amount of bone removal at the facet joints (FJ5a,b). The width of the fusion cage 12 as measured between the superior and inferior saddle portions 28, 32 (trough to trough) may be provided in a multitude of sizes, such as 8-20 mm in single mm. increments. It is contemplated that such dimensions may be largely anatomy controlled.

The method may further include positioning the fusion cage 12 with the interspinious surface 22 generally aligned with the lamina (LA4a-b and LA5a-b), and the thecal sac surface 26 aligned with the thecal sac (TS). With this positioning it is contemplated that the superior openings 42*a*-*c* may be exposed to the adjacent vertebra (L4) and in particular the superior spinolaminar junction (SSJ) and lamina (LA4a-b). Further, the inferior openings 44*a*-*c* may be exposed to the adjacent vertebra (L5), and in particular the inferior spinolaminar junction (ISJ) and lamina (L54a-b). In addition, the facet openings 42*a*, *b* may be exposed to the adjacent facet joints (FJ5a-b).

As described above, the fusion cage 12 may include a cage recess 40. The cage recess 40 may be packed with a boney fusion mass (BFMa) (actual and/or artificial) to facilitate fusion between the fusion cage 12 and the adjacent vertebrae (L4, L5). The superior openings 42*a*-*c*, the inferior openings 44*a*-*c*, and the facet openings 42*a*-*b* may all expose the packed boney fusion mass for contact with the adjacent vertebrae (L4, L5) for fusion at such locations of exposure.

Figure 7B:
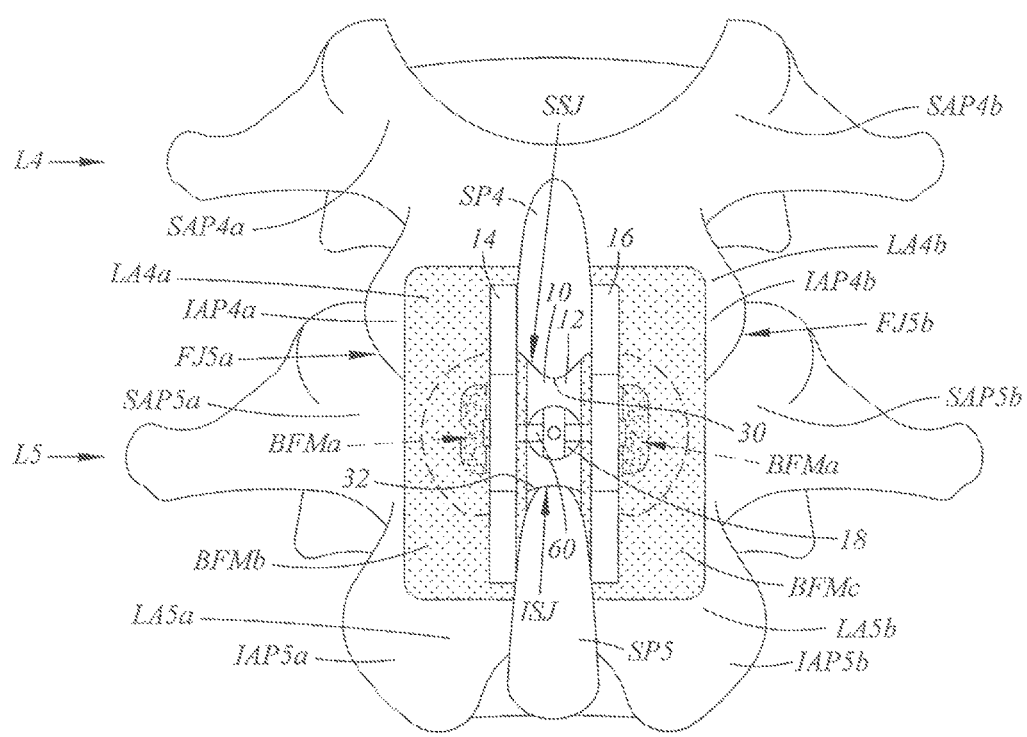
FIG. 7b is the posterior view illustrating the lumbar region of the spine of FIG. 6b with a boney mass positioned over the fusion cage and the lamina of the adjacent vertebrae.
Figure 9B:
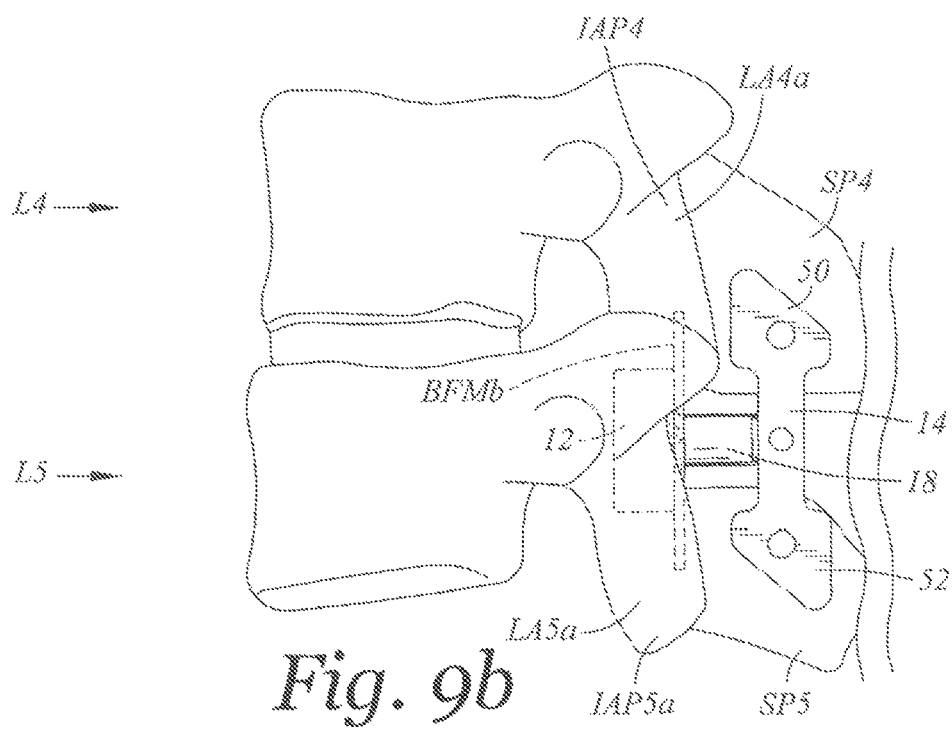
FIG. 9b is the side view illustrating the L4 and L5 vertebrae of FIG. 9a with the spinal implant device installed and a boney mass positioned over the fusion cage and the lamina of the adjacent vertebrae ((portions of which shown in phantom)

Referring now to FIG. 7*b* there is depicted the posterior view illustrating the lumbar region of the spine of FIG. 6*b* with a boney fusion mass (BFMb-c) positioned over the fusion cage 12 and the lamina (LA4a-b and LA5a-b) of the adjacent vertebrae (SP4, SP5). The boney fusion mass (BFMb) is also depicted in FIG. 9*b* (shown in phantom). The interspinous surface 22 with the interspinous openings 48*a*-*b* therein extending to the cage recess 40 and the boney fusion mass packed therein. It is contemplated that the interspinous openings 48*a*-*b* allow for contact and fusion with the boney fusion mass (BFMa) and the boney fusion mass (BFMb-c). In this regard, the method may further include disposing a boney fusion mass (BFMb-c) in contact with the superior lamina (LA4a-b) and the inferior lamina (LA5a-b) across and in contact with the boney fusion mass (BFMa) within the fusion cage 12.

The method may include using a fastener, such as fasteners 82, 90, to compress the first and second fixation plates 14, 16 to the adjacent spinous processes (SP4, SP5) with the spinous processes (SP4, SP5) disposed between the fixation plates 14, 16. In addition, the method may further include attaching the fixation plates 14, 16 to the spinous processes (SP4, SP5) with screws. Such an embodiment is discussed further below.

Figure 10A:
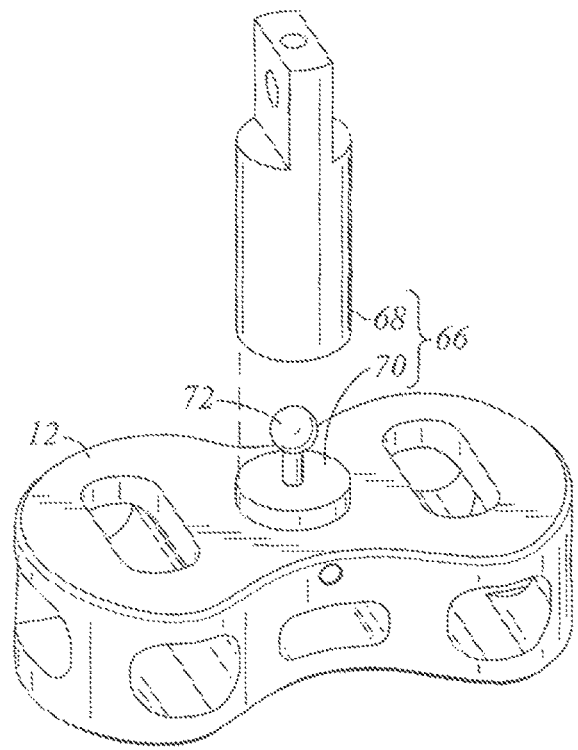
FIG. 10a is an exploded perspective view of a portion of a spinal implant device having a fusion cage and a connector with a ball joint according to another embodiment.
Figure 10B:
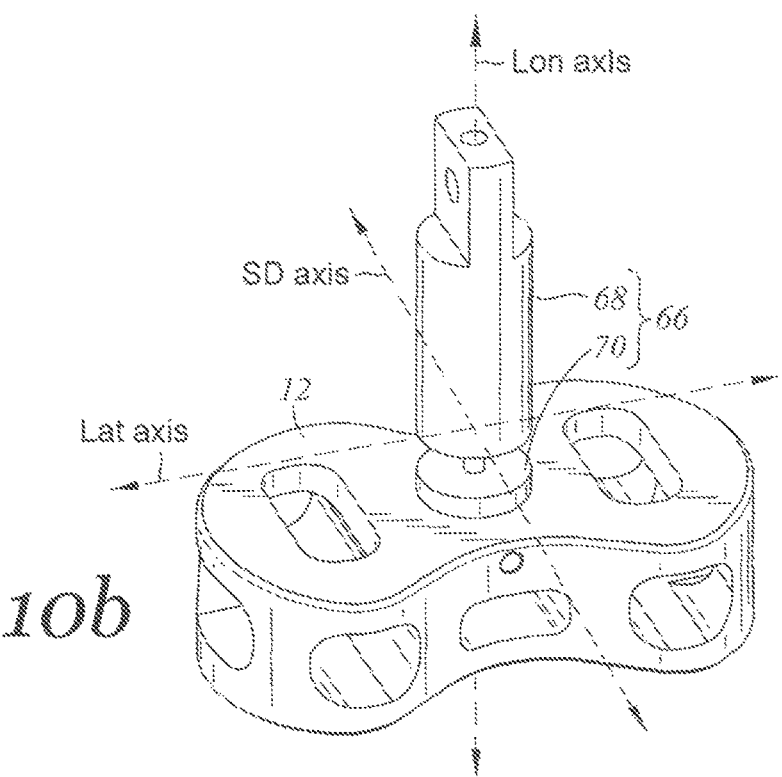

Referring now to FIG. 10*a*, there is depicted an exploded perspective view of a portion of a spinal implant device according to another embodiment similar to the spinal implant device 10. Like reference numerals indicate like structures. Thus, similar referenced structures are as described above but with those differences noted. In this embodiment, there is provided a connector 66 that may be connected to the fusion cage 12 (as described above). FIG. 10*b* is an assembled view of the portion of the spinal implant device of FIG. 10*a*. The connector 66 includes a shaft 68 and a base 70. The base 70 further includes a ball joint 72. The shaft 68 includes a recess (not shown) sized and configured to receive the ball joint 72. The connector 66 defines a longitudinal axis (Lon axis). With the connector 66 assembled, the connector 66 is rotatably connected to the fusion cage 12 with respect to rotation about the longitudinal axis (Lon axis). Further, the connector 66 may be pivotably connected to the fusion cage 12 with respect to pivoting about an axis other than the longitudinal axis (Lon axis), such as with respect to any combination of pivoting with regard to a lateral axis (Lat axis) and a superficial/deep axis (SD axis) which are disposed orthogonal to the longitudinal axis (Lon axis) and each other. For example, it is contemplated that the connector 66 may be constrained to only rotate about the Lon axis and pivot about the Lat axis. It is contemplated that other arrangements for limiting the extent of or number of degrees of freedom in which the connector 68 may be implemented may be chosen from those which are well know to one of ordinary skill in the art.

Figure 11:
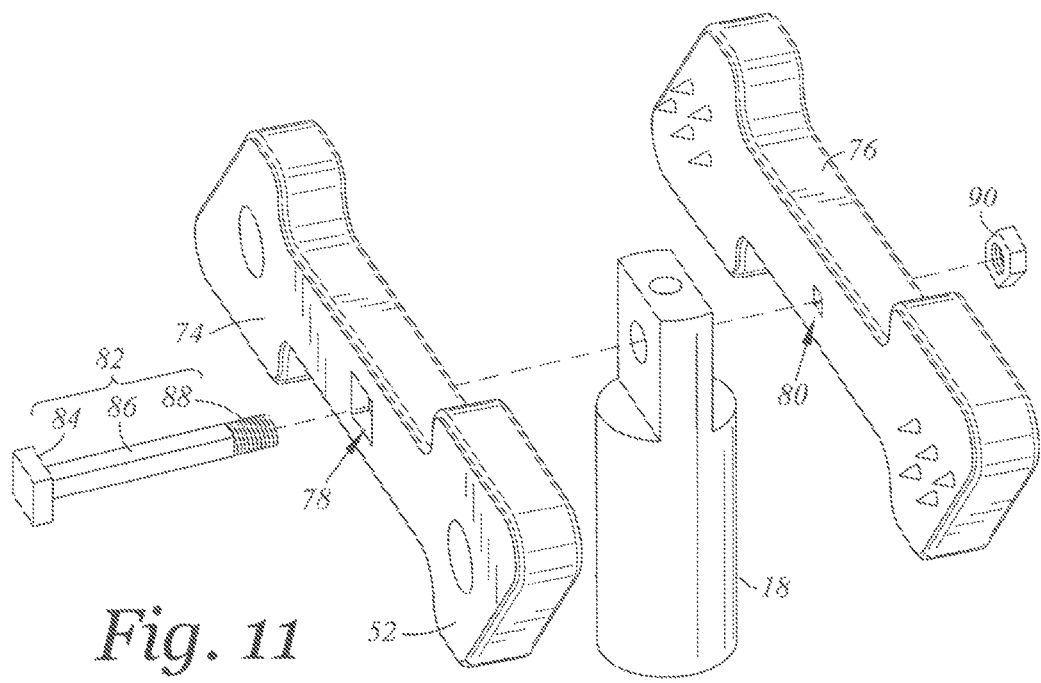
FIG. 11 is an exploded perspective view of portion of a spinal implant device having a connector, first and second fixation plates and fastener connecting the connector and the plates according to another embodiment.

Referring now to FIG. 11 there is depicted an exploded perspective view of portion of a spinal implant device according to another embodiment having first and second fixation plates 74, 76 and a fastener 82 that is used to connect the first and second fixation plates 74, 76 to the connector 18. The connector 18 is a described above and is contemplated to be attached to the fusion cage 12 also as described above. Like reference numerals indicate like structures. Thus, similar referenced structures are as described above, but with those differences noted.

The first and second fixation plates 74, 76 are similar to the first and second fixation plates 14, 16 described above. However, in this embodiment, the first fixation plate 74 includes a fastener hole 78 and the second fixation plate 76 includes a fastener hole 80. A fastener 82 is provided that includes a head 84, a shaft 86 and a threaded end 88. The fastener shaft 86 is contemplated to extend through the fastener hole 78, the connector 18 and the fastener hole 80. The head 84 is of a non-circular cross-section, and, in this embodiment the head 84 has a square cross-section. The head 84 is sized and configured to engage the fastener hole 78 to prevent rotation of the head 84 when engaged with the fastener hole 78. The shaft 86 is also of a non-circular cross-section, and in this embodiment the shaft 86 has a square cross-section. The shaft 86 is configured to engage the fastener hole 80 to prevent rotation of the shaft 86 when engaged with the fastener hole 80. In this embodiment, the first and second fixation plates 74, 76 are configured to pivot in unison with regard to the connector 18. In this regard, the particular non-circular nature of the cross-sections of the fastener head 84 and the shaft 86 facilitate engagement with the first and second fixation plates 74, 76 to lock relative movement. Also in this embodiment, the threaded end 88 of the fastener 82 is sized and configured to threadedly engage a nut 90. In this regard the connector 18 may be connected to the first and second fixation plates 74, 76 with the fastener 82 sized and configured to compress the first and second fixation plates 74, 76 against the spinous processes (SP4, SP5).

Figure 12:
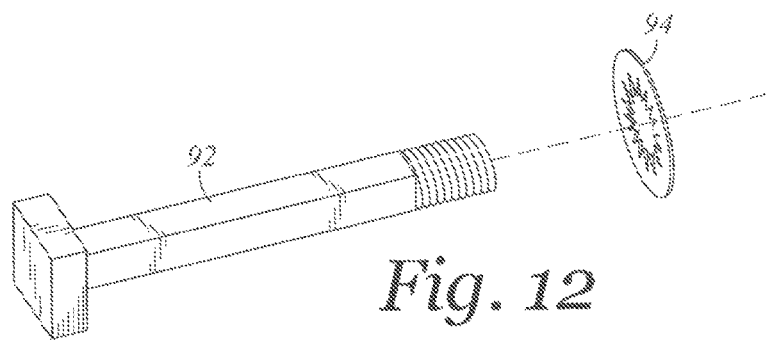
FIG. 12 is an exploded view of a fastener according to another embodiment.

FIG. 12 is a perspective view of a fastener 92 according to another embodiment. It is contemplated that the fastener 92 may be used in place of the fastener 82 described above. In this embodiment, rather than using a nut 90, a lock washer 94 is provided that is sized and configured to engage the fastener 92 that includes a ribbed end. As one of ordinary skill in the art will appreciate, the selection of the fastener 92 over the fastener 82 would depend upon the torque strength requirements of the fastener application.

Figure 13A:
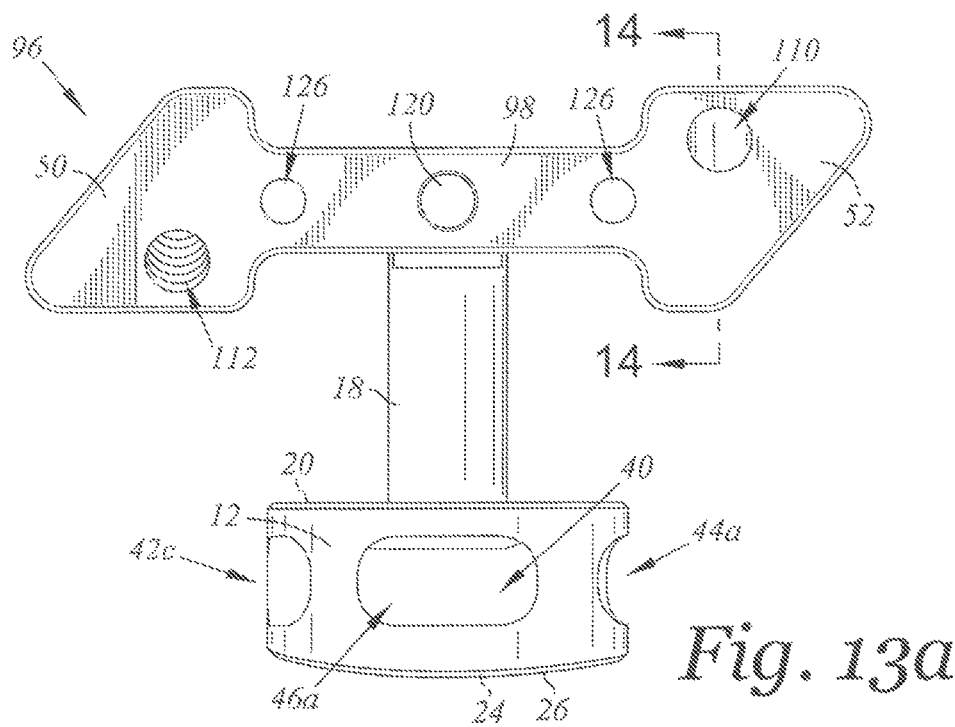
FIG. 13a is a side view of a spinal implant device according to another embodiment.
Figure 13B:
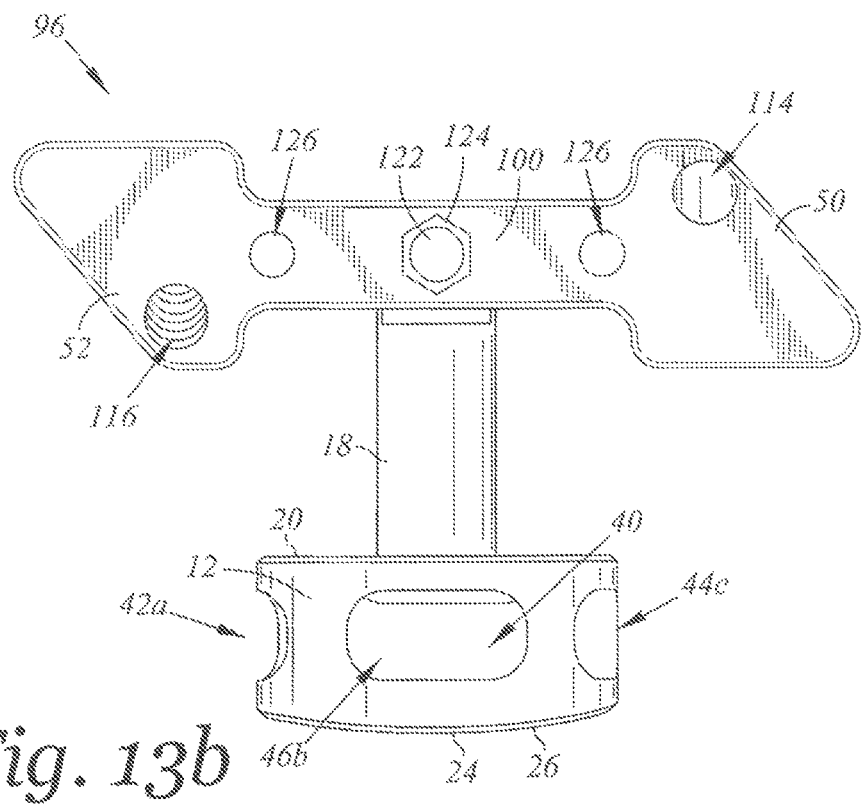
Figure 14:
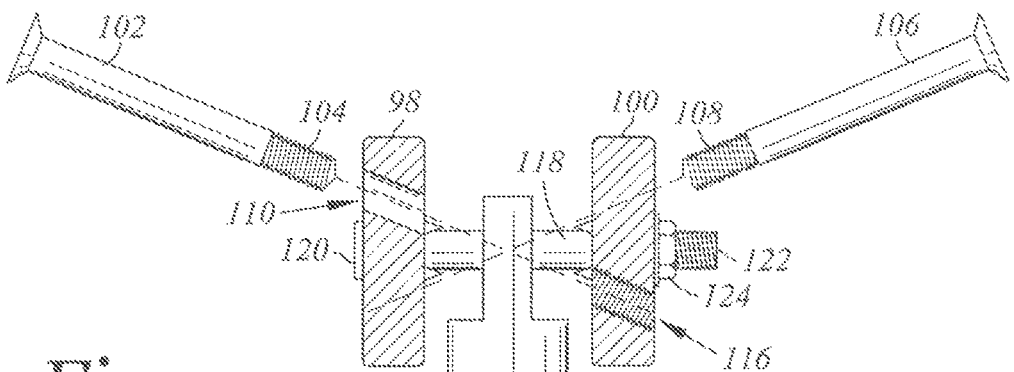
FIG. 14 is an exploded end view of the spinal implant device of FIG. 13a with lag screws as seen along axis 14-14.

Referring now to FIGS. 13*a-b* and 14 there is depicted a spinal implant device 96 according to another embodiment. FIG. 13*a* is a side view of the spinal implant device 96, and FIG. 13*b* is a reverse side view of the spinal implant device 96. FIG. 14 is an exploded end view of the spinal implant device 96 of FIG. 13*a* as viewed along axis A-A with first and second fixation plates 98, 100 configured to engage lag screws 102, 106. Like reference numerals indicate like structures. Thus, similar referenced structures are as described above, but with those differences noted. The spinal implant device 96 includes first and second fixation plates 98, 100 are similar to the first and second fixation plates 14, 16 described above. However, in this embodiment, the first and second fixation plates 98, 100 respectively include screw holes 110, 112, 114, 116 that are disposed at an oblique angle through the first and second fixation plates 98, 100. It is contemplated that such angulation allows for an ease for the surgeon to insert the screws (as opposed to being inserted laterally which may require additional anatomical structures and matter to be disturbed).

The lag screw 102 includes a threaded end 104, and the lag screw 106 includes a threaded end 106. The screw holes 112, 116 are threaded and cooperatively sized and configured to respectively threadedly engage the threaded ends 104, 108 of the lag screws 102, 106. The screw hole 110 is configured to receive the lag screw 102 there the screw hole 110, and the screw hole 114 is configured to receive the lag screw 104 there the screw hole 114.

As such during installation, the lag screw 102 may be inserted through the screw hole 110, through the spinous process (such as SP5), and into the screw hole 116. Likewise, the lag screw 104 may be inserted through the screw hole 114, through the spinous process (such as SP4), and into the screw hole 112. It is contemplated that by screwing the lag screws 102, 106 respectively into the screw holes 116, 112 the first and second fixation plates 98, 100 are drawn toward each other. Moreover, the first and second fixation plates 98, 100 may be thus be configured to apply a compressive force against the spinous processes (SP4, SP5) to lock the first and second fixation plates 98, 100 in place and to provide fixation for the connected fusion cage 12. In this embodiment, there is provided a pin 118 with an end cap 120 and a threaded end 122. The threaded end 122 is sized and configured to engage a nut 124. The first and second fixation plates 98, 100 further includes indexing features 126. The indexing features 126 are similar to the indexing features 64 of the embodiment discussed above.

Relative spacing between the first and second fixation plates 98, 100 is dictated to a large degree by the angle and placement in which the screw holes 110, 112, 114, 116 are formed respectively with regard to the first and second fixation plates 98, 100. As such, it is contemplated that the surgeon would have an array of similarly configured spinal implant devices 96 with differing spacing between the first and second fixation plates 98, 100 (with corresponding differing angulations and/or placement of the screw holes 110, 112, 114, 116). As such, after the surgeon has created the necessary surgical window discussed above, a particular spinal implant device 96 may be chosen in reference to the width requirements associated with the spinous processes (SP4, SP5).

In addition, the method of installing the spinal implant device 96 may include attaching the fixation plates 98, 100 to the spinous processes (SP4, SP5) with the lag screws 104, 106. The method includes positioning the first and second fixation plates 98, 100 in their desired position with regard to the spinous processes (SP4, SP5). The pin 118 is then inserted through the first fixation plate 98, through the connector 10 and through the second fixation plate 100. The nut 124 is then engaged with the threaded end 122 of the pin 118.

The method may further include inserting the lag screws 102, 104. Prior to such insertion, the method would further include drilling a hole through each of the spinous processes (SP4, SP5). To facilitate such drilling, a drill guide (not depicted) may be provided that is engaged with the first fixation plate at the screw hole 110. The drill guide is contemplated to aid in maintaining a drill bit at a desired angle so as to align the drill bit with the screw holes 110, 116. The method would thus include inserting the drill bit through the drill guide through the first fixation plate, into and through the spinous process (SP5), and into the screw hole 116. The lag screw 102 may then be inserted through first fixation plate 98, through the spinous process (SP5), and through the second fixation plate 100. The lag screw 102 is then screwed into the second fixation plate 100 with the threaded end 104 engaging the screw hole 116. A like process would be performed with regard to the lag screw 106, the screw holes 114, 112, and the spinous process (SP4).

Figure 15:
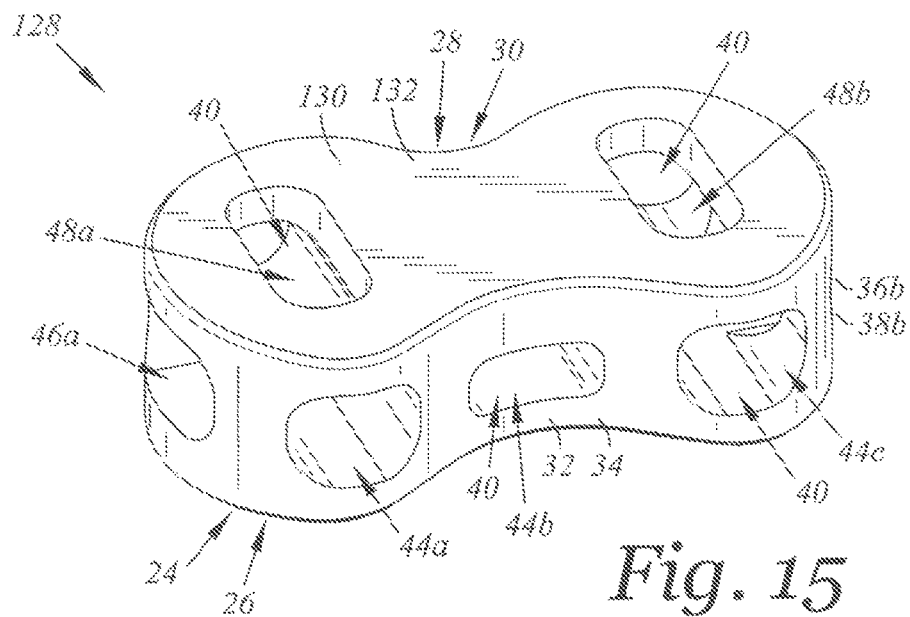
FIG. 15 is a perspective view of a spinal implant device according to another embodiment of the invention that includes a fusion cage.

Referring now to FIG. 15 there is depicted a perspective view of a spinal implant device 128 according to another embodiment of the invention. In this embodiment the spinal implant device 128 takes the form of a fusion cage, similar to the fusion cage 12 of the spinal implant device 10.

However, in this embodiment, the spinal implant device 128 does not required the fixation features of the spinal implant device 10 (i.e., a connector and fixation plates). Like reference numerals indicate like structures. Thus, similar referenced structures are as described above but with those differences noted. The spinal implant device 128 includes a superficial face 130 that defines a interspinous surface 132. Spinal implant device 128 is contemplated to provide a fusion capability similar to that of the spinal implant device 10 described above. However, in this embodiment, the first spinal implant device 128 allow for the flexibility to employ other fixation techniques, such as any of those which may be chosen from those which are well known to one of ordinary skill in the art.

The particulars shown herein are by way of example only for purposes of illustrative discussion, and are presented in the cause of providing what is believed to be the most useful and readily understood description of the principles and conceptual aspects of the various embodiments set forth in the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A spinal implant device for use with adjacent spinous processes, the spinous processes including a superior spinous process and an inferior spinous process, the spinal implant device comprising:
    a first fixation plate including a first superior end and a first inferior end, the first superior end including a first screw hole extending through the first fixation plate at a fixed angle therethrough, the first fixation plate being sized and configured to extend between and along the spinous processes with the first screw hole adjacent the superior spinous process;
    a second fixation plate including a second superior end and a second inferior end, the second inferior end including a second screw hole extending through the second fixation plate at a fixed angle therethrough, the second fixation plate being sized and configured to extend between and along the spinous processes with the second screw hole adjacent the inferior spinous process;
    a connector connected to the first fixation plate between the first superior end and the first inferior end and to the second fixation plate between the second superior end and the second inferior end;
    a first screw sized and configured to extend through the first screw hole along the fixed angle of the first screw hole towards and in a direction intersecting with the second fixation plate with the superior spinous process disposed between the first and second superior ends; and
    a second screw sized and configured to extend through the second screw hole along the fixed angle of the second screw hole towards and in a direction intersecting with the first fixation plate with the inferior spinous process disposed between the first and second inferior ends, the first and second screws being angularly disposed and non-parallel with respect to each other.

2. The spinal implant device of claim 1 wherein the first fixation plate includes a third screw hole adjacent the inferior spinous process, the second fixation plate includes a fourth screw hole adjacent the superior spinous process, the fourth screw hole is threaded, the first screw is sized and configured to extend through the first screw hole and threadedly engage the fourth screw hole with the superior spinous process disposed between the first and second superior ends.

3. The spinal implant device of claim 2 wherein the second screw hole is threaded, the second screw is sized and configured to extend through the second screw hole and threadedly engage the third screw hole with the inferior spinous process disposed between the first and second inferior ends.

4. The spinal implant device of claim 1 wherein the first fixation plate is generally planar and defining a superficial/deep plane, the first screw hole extends through the first fixation plate at an angle less than 90 degrees with respect to the superficial/deep plane.

5. The spinal implant device of claim 1 wherein the first and second fixation plates are each generally planar and each define a superficial/deep plane, the first and second fixation plates are configured to translate relative to each other along a lateral axis orthogonal to the superficial/deep planes.

6. The spinal implant device of claim 1 wherein the first and second fixation plates are angularly in fixed relation to each other.

7. The spinal implant device of claim 1 wherein the connector is a pin.

8. The spinal implant device of claim 1 wherein the connector in the slidable engagement with the second fixation plate.

9. The spinal implant device of claim 1 wherein the connector has a noncircular cross-section.

10. The spinal implant device of claim 1 wherein the connector is in fixed relation to the first fixation plate.

11. The spinal implant device of claim 1 wherein the first and second fixation plates each include teeth for respectively engaging the spinous processes.

12. A method of implanting a spinal implant device for placement between adjacent spinous processes, the spinous processes including a superior spinous process and an inferior spinous process, the method comprising:
    a) providing the spinal implant device including first and second fixation plates, the first fixation plate including a first superior end and a first inferior end, the first superior end including a first screw hole extending through the first fixation plate at a fixed angle therethrough, the second fixation plate including a second superior end and a second inferior end, the second inferior end including a second screw hole extending through the second fixation plate at a fixed angle therethrough;
    b) positioning the first fixation plate along the spinous processes with the first superior end adjacent the superior spinous process and the first inferior end adjacent the inferior spinous process;
    c) positioning the second fixation plate along the spinous processes with the second superior end adjacent the superior spinous process and the second inferior end adjacent the inferior spinous process;
    d) inserting a first screw through the first screw hole along the fixed angle of the first screw hole towards the second fixation plate and into the superior spinous process; and
    e) inserting a second screw through the second screw hole along the fixed angle of the second screw hole towards the first fixation plate and into the inferior spinous process with the first and second screws being angularly disposed and non-parallel with respect to each other and with respect to axes extending transverse to surfaces of the first and second plates configured to face the spinous processes.

13. The method of claim 12 wherein the first fixation plate is generally planar and defining a superficial/deep plane, the first screw hole extends through the first fixation plate at an angle less than 90 degrees with respect to the superficial/deep plane.

14. The method of claim 12 wherein the first and second fixation plates are each generally planar and each define a superficial/deep plane, further comprising translating at least one of the first and second fixation plates relative to the other of the first and second fixation plates along a lateral axis orthogonal to the superficial/deep planes.

15. The method of claim 12 wherein the first and second fixation plates are angularly in fixed relation to each other.

16. The method of claim 12, further comprising engaging the spinous processes with teeth extending from the first and second fixation plates.

* * * * *